(12) United States Patent
Blasko et al.

(10) Patent No.: US 7,247,627 B2
(45) Date of Patent: Jul. 24, 2007

(54) SALTS AND POLYMORPHS OF A PYRROLE-SUBSTITUTED INDOLINONE COMPOUND

(75) Inventors: Andrei Blasko, San Bruno, CA (US); Qingwu Jin, Palo Alto, CA (US); Qun Lu, Portage, MI (US); Michael A. Mauragis, Scotts, MI (US); Dian Song, Redwood City, CA (US); Brenda S. Vonderwell, Plainwell, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 224 days.

(21) Appl. No.: 10/956,420

(22) Filed: Sep. 30, 2004

(65) Prior Publication Data

US 2005/0118255 A1 Jun. 2, 2005

Related U.S. Application Data

(60) Provisional application No. 60/508,104, filed on Oct. 2, 2003.

(51) Int. Cl.
*A61K 31/5377* (2006.01)
*C07D 413/14* (2006.01)

(52) U.S. Cl. ............. 514/235.2; 544/106; 544/111; 544/141; 544/144; 514/231.2; 514/232.8; 514/233.5

(58) Field of Classification Search ............ 544/106, 544/111, 141, 143, 144; 514/231.2, 232.8, 514/233.5, 235.2
See application file for complete search history.

(56) References Cited

U.S. PATENT DOCUMENTS

| 6,573,293 | B2 | 6/2003 | Tang et al. |
| 6,653,308 | B2 | 11/2003 | Guan et al. |
| 2003/0069298 | A1 | 4/2003 | Hawley et al. |
| 2003/0092914 | A1 | 5/2003 | Guan et al. |
| 2003/0229229 | A1 | 12/2003 | Jin et al. |

FOREIGN PATENT DOCUMENTS

| WO | WO02/066463 | 8/2002 |
| WO | WO2004/024127 | 3/2004 |

*Primary Examiner*—Golam M. M. Shameem
(74) *Attorney, Agent, or Firm*—Ye Hua; Stephen D. Prodnuk; Bryan C. Zielinski

(57) ABSTRACT

The invention relates to non-hygroscopic salts of 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide, such as maleate salts, and to crystalline polymorphs of these salts. The invention further relates to pharmaceutical compositions of 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide salts, and methods of treating disorders such as cancer using such compositions.

9 Claims, 19 Drawing Sheets

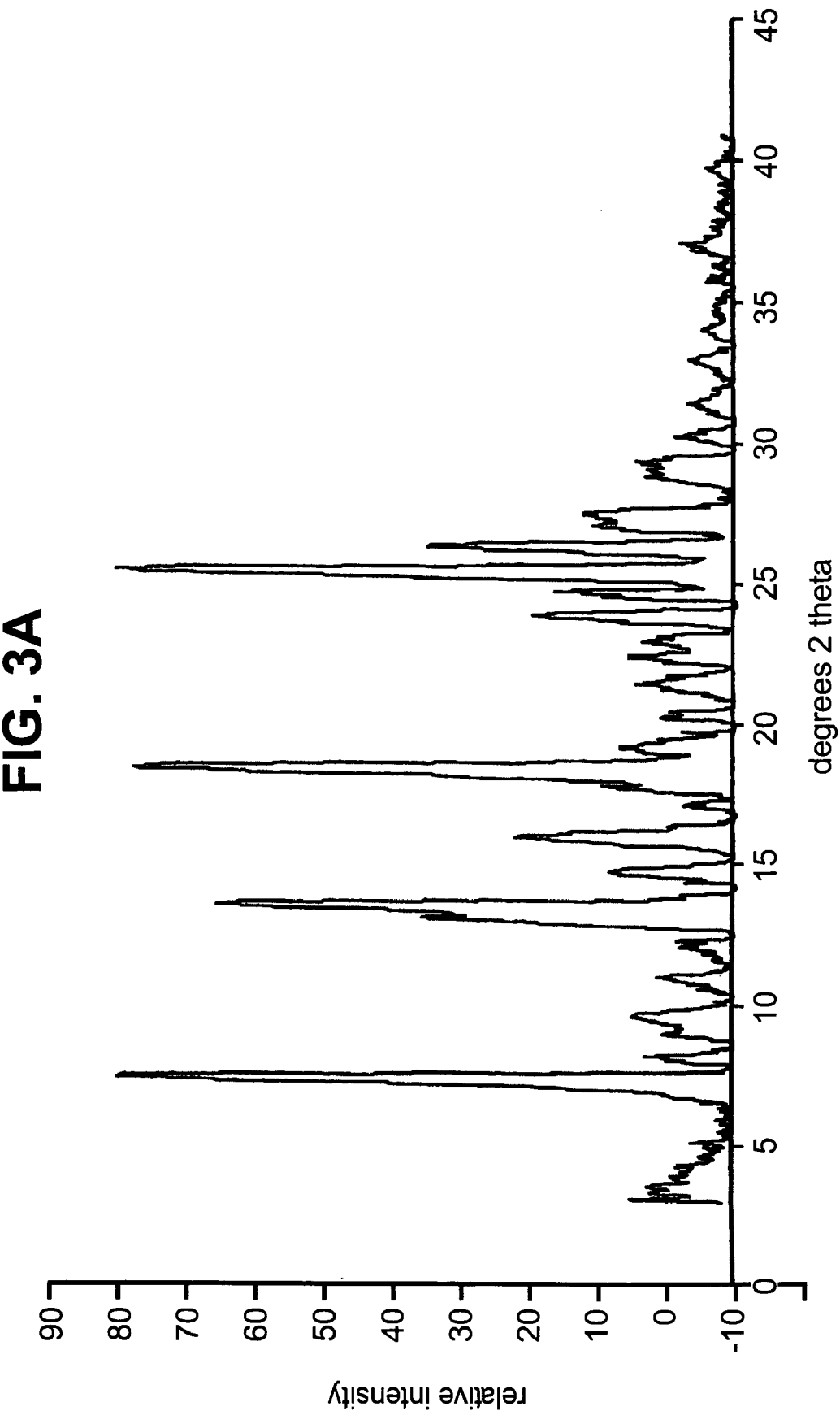

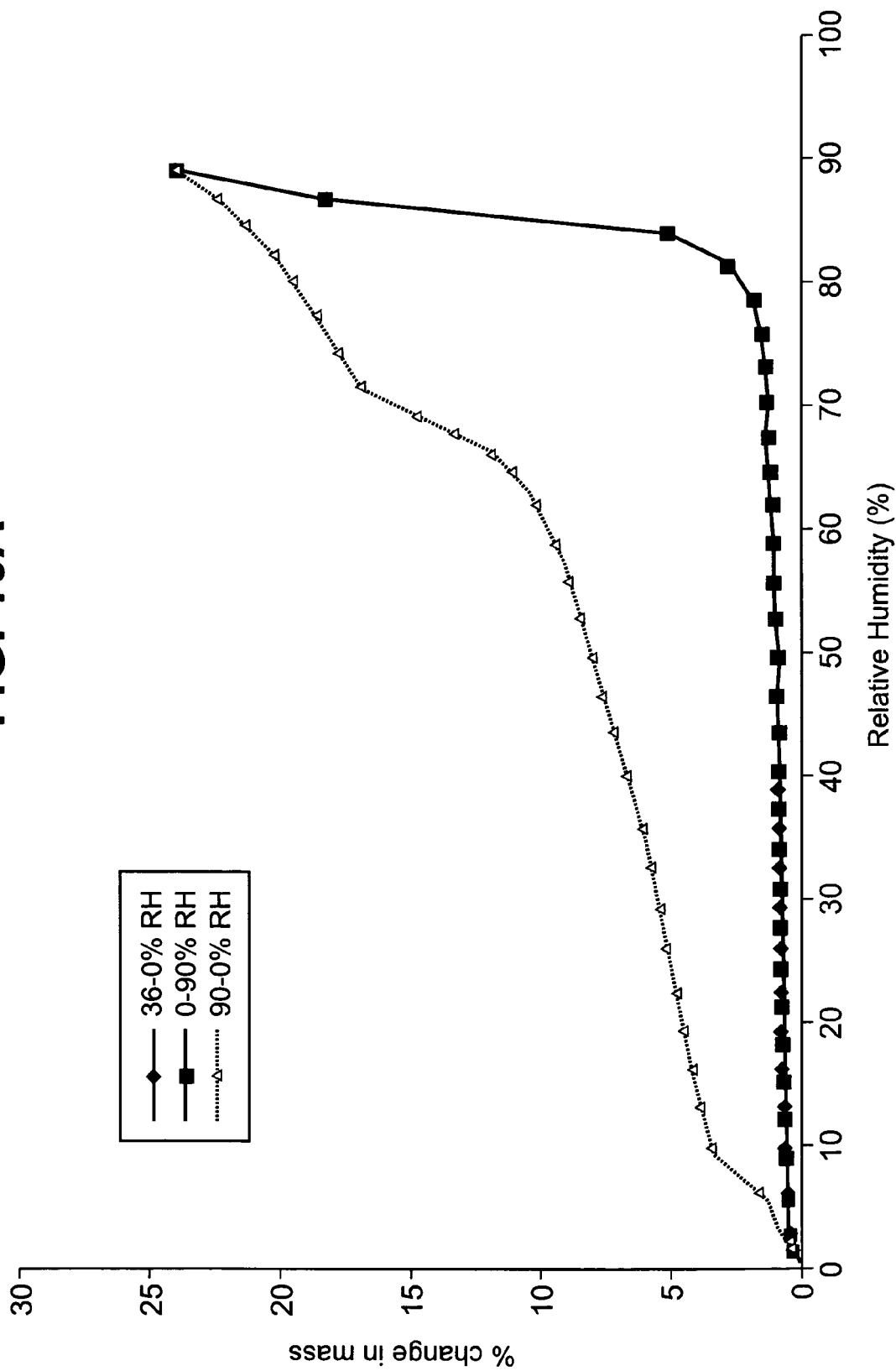

SALTS AND POLYMORPHS OF A PYRROLE-SUBSTITUTED INDOLINONE COMPOUND

This application claims the benefit of U.S. Provisional Application Ser. No. 60/508,104, filed Oct. 2, 2003, the disclosure of which is incorporated herein by reference in its entirety.

BACKGROUND OF THE INVENTION

This invention relates to salt forms and polymorphs of 5-[(Z)-(5-fluoro-2-oxo-1,2-dihydro-3H-indol-3-ylidene) methyl]-N-[(2S)-2-hydroxy-3-morpholin-4-ylpropyl]-2,4-dimethyl-1H-pyrrole-3-carboxamide that are useful in the treatment of abnormal cell growth, such as cancer, in mammals. This invention also relates to compositions including such salts, and to methods of using such compositions in the treatment of abnormal cell growth in mammals, especially humans.

The compound 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide, shown in structural formula 1, is a potent, selective oral inhibitor of receptor tyrosine kinases (RTKs) involved in

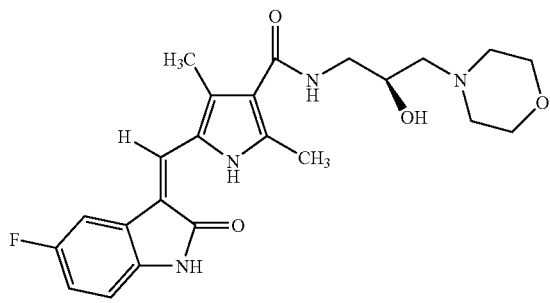

1 signaling cascades that trigger tumor growth, progression and survival. In vivo studies have shown that this compound has anti-tumor activity in diverse preclinical solid and hematopoietic cancer xenograft models. This compound, its preparation and use are further described in U.S. patent application publication No. US 2003/0092917, published May 15, 2003, the disclosure of which is incorporated herein by reference in its entirety.

In its free base form, 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide is fairly crystalline, chemically and enantiomerically stable, and relatively non-hygroscopic. However, it would be advantageous to have salt forms having improved properties, such as improved crystallinity and/or decreased hygroscopicity, while maintaining chemical and enantiomeric stability properties.

SUMMARY OF THE INVENTION

In one embodiment, the invention provides a non-hygroscopic salt of 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide. Hygroscopicity is determined by dynamic moisture sorption gravimetry (DMSG) using a controlled atmosphere microbalance at a temperature of 25° C. Samples are analyzed over a relative humidity range of from 0 to 90% in 3% steps. Each step is brought to equilibrium before moving to the next step, with equilibrium assessed as a weight change of less than 0.002 mg (0.02%) for five consecutive points at 1 point per 120 seconds. Using this measure of hygroscopicity, non-hygroscopic salts of the invention exhibit a water uptake of less than 5%, preferably less than 4%, more preferably less than 3%, more preferably less than 2%, more preferably less than 1% by weight, at 80% relative humidity.

In particular aspects of this embodiment, the salt is anhydrous, crystalline, or both anhydrous and crystalline.

In a particular aspect of this embodiment, the salt is a maleate salt, preferably an anhydrous maleate salt or a crystalline maleate salt, more preferably a crystalline anhydrous maleate salt.

In particular aspects of this embodiment, the salt is a crystalline anhydrous maleate salt of polymorphic Form 1 or polymorphic Form 2.

Polymorphic Form 1 is a crystalline, anhydrous polymorph having characteristic powder X-ray diffraction (PXRD) peaks at diffraction angles (2θ) of 12.7 and 15.4°. More particularly, polymorph Form 1 has a PXRD pattern including peaks as shown in Table 1.

TABLE 1

| Polymorph Form 1 PXRD | |
|---|---|
| 2θ (°) | I/I$_{max}$ (%) |
| 10.85 | 15 |
| 12.68 | 20 |
| 14.48 | 13 |
| 15.35 | 41 |
| 17.06 | 17 |
| 18.14 | 100 |
| 19.04 | 58 |
| 20.18 | 14 |
| 20.42 | 16 |
| 22.37 | 68 |
| 24.74 | 52 |
| 25.73 | 25 |
| 26.84 | 44 |
| 27.41 | 53 |

One skilled in the art will appreciate that the peak positions (2θ) will show some inter-apparatus variability, typically as much as 0.1°. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measures only. Still more particularly, polymorph Form 1 has a PXRD pattern essentially the same as shown in FIG. 1, where "essentially the same" encompasses typical peak position and intensity variability as discussed above.

Polymorphic Form 2 is a crystalline, anhydrous polymorph having characteristic powder X-ray diffraction (PXRD) peaks at diffraction angles (2θ) of 13.1 and 15.9°. More particularly, polymorph Form 2 has a PXRD pattern including peaks as shown in Table 2.

TABLE 2

Polymorph Form 2 PXRD

| 2θ (°) | I/I$_{max}$ (%) |
|---|---|
| 7.31 | 6 |
| 10.97 | 35 |
| 11.87 | 26 |
| 13.10 | 17 |
| 14.63 | 43 |
| 15.89 | 100 |
| 17.42 | 39 |
| 18.14 | 87 |
| 18.98 | 39 |
| 19.52 | 28 |
| 20.30 | 28 |
| 22.28 | 46 |
| 22.82 | 41 |
| 23.96 | 34 |
| 24.56 | 67 |
| 25.88 | 47 |
| 27.02 | 44 |

Still more particularly, polymorph Form 2 has a PXRD pattern essentially the same as shown in FIG. 2, where "essentially the same" encompasses typical peak position and intensity variability as discussed above.

In another aspect of this embodiment, the salt is a crystalline anhydrous maleate salt of polymorphic Form 1 or polymorphic Form 2, wherein the polymorphic form is substantially pure. A "substantially pure" salt of polymorphic Form 1 includes less than 10%, preferably less than 5%, preferably less than 3%, preferably less than 1% by weight of polymorph Form 2 or any other polymorphic form. Similarly, a "substantially pure" salt of polymorphic Form 2 includes less than 10%, preferably less than 5%, preferably less than 3%, preferably less than 1% by weight of polymorph Form 1 or any other polymorphic form.

In another aspect of this embodiment, the salt is a crystalline anhydrous maleate salt that is a mixture of polymorphic Form 1 and polymorphic Form 2. Preferably, the mixture is a substantially pure mixture, where a substantially pure mixture of polymorphic forms 1 and 2 includes less than 10%, preferably less than 5%, preferably less than 3%, preferably less than 1% by weight of any other polymorphic forms.

Mixtures of polymorph forms 1 and 2 will have diffraction peaks characteristic of both forms, particularly peaks at diffraction angles (2θ) of 12.7, 13.1, 15.4 and 15.9, more particularly peaks at the positions shown in Tables 1 and 2, still more particularly a PXRD pattern that is a convolution of FIGS. 1 and 2.

In another embodiment, the invention provides a maleate salt of 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide.

In particular aspects of this embodiment, the maleate salt is crystalline, anhydrous, or both crystalline and anhydrous.

In particular aspects of this embodiment, the maleate salt is a crystalline anhydrous salt of polymorph Form 1, preferably substantially pure polymorph Form 1, or polymorph Form 2, preferably substantially pure polymorph Form 2, or a mixture of polymorph forms 1 and 2, preferably a substantially pure mixture, where polymorph forms 1 and 2 are as described above.

In another embodiment, the invention provides a crystalline anhydrous maleate salt of 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide. In particular aspects of this embodiment, the crystalline anhydrous maleate salt is a salt of polymorph Form 1, preferably substantially pure polymorph Form 1, or polymorph Form 2, preferably substantially pure polymorph Form 2, or a mixture of polymorph forms 1 and 2, preferably a substantially pure mixture, where polymorph forms 1 and 2 are as described above.

In another embodiment, the invention provides a crystalline anhydrous maleate salt of 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide having a powder X-ray diffraction pattern comprising peaks at diffraction angles (2θ) essentially the same as shown in FIG. 1, where "essentially the same" is as defined above.

In another embodiment, the invention provides a crystalline anhydrous maleate salt of 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide having a powder X-ray diffraction pattern comprising peaks at diffraction angles (2θ) essentially the same as shown in FIG. 2, where "essentially the same" is as defined above.

In another embodiment, the invention provides a crystalline anhydrous maleate salt of 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide having a powder X-ray diffraction pattern which is a convolution of diffraction patterns comprising peaks at diffraction angles (2θ) essentially the same as shown in FIGS. 1 and 2, where "essentially the same" is as defined above.

In another embodiment, the invention provides a pharmaceutical composition comprising the salt of any of the preceding embodiments.

In another embodiment, the invention provides a capsule comprising any of the pharmaceutical compositions of the invention. In particular aspects of this embodiment, the capsule comprises from 5 to 75 mg, preferably from 10 to 25 mg, free base equivalent of the 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide salt.

In another embodiment, the invention provides a method of treating cancer in a mammal, including a human, the method comprising administering to the mammal a therapeutically effective amount of any of the pharmaceutical compositions of the invention.

In another embodiment, the invention provides a method of treating cancer in a mammal, the method comprising administering to the mammal, including a human, any of the capsules of the invention.

In a particular aspect of any of the preceding method embodiments, the method further comprises administering one or more anti-tumor agents, anti-angiogenesis agents, signal transduction inhibitors, or antiproliferative agents.

The invention also relates to a method for the treatment of abnormal cell growth in a mammal, including a human, comprising administering to said mammal an amount of a compound of the formula 1, as defined above, or a pharmaceutically acceptable salt, solvate or prodrug thereof, that is effective in treating abnormal cell growth. In one embodiment of this method, the abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said method, said abnormal cell growth is a benign proliferative disease, including, but not limited to, psoriasis, benign prostatic hypertrophy or restinosis.

This invention also relates to a method for the treatment of abnormal cell growth in a mammal which comprises administering to said mammal an amount of a compound of formula 1, or a pharmaceutically acceptable salt, solvate or prodrug thereof, that is effective in treating abnormal cell growth in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

This invention also relates to a pharmaceutical composition for the treatment of abnormal cell growth in a mammal, including a human, comprising an amount of a compound of the formula 1, as defined above, or a pharmaceutically acceptable salt, solvate or prodrug thereof, that is effective in treating abnormal cell growth, and a pharmaceutically acceptable carrier. In one embodiment of said composition, said abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said pharmaceutical composition, said abnormal cell growth is a benign proliferative disease, including, but not limited to, psoriasis, benign prostatic hypertrophy or restinosis.

The invention also relates to a pharmaceutical composition for the treatment of abnormal cell growth in a mammal, including a human, which comprises an amount of a compound of formula 1, as defined above, or a pharmaceutically acceptable salt, solvate or prodrug thereof, that is effective in treating abnormal cell growth in combination with a pharmaceutically acceptable carrier and an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

This invention also relates to a method for the treatment of a disorder associated with angiogenesis in a mammal, including a human, comprising administering to said mammal an amount of a compound of the formula 1, as defined above, or a pharmaceutically acceptable salt, solvate or prodrug thereof, that is effective in treating said disorder. Such disorders include cancerous tumors such as melanoma; ocular disorders such as age-related macular degeneration, presumed ocular histoplasmosis syndrome, and retinal neovascularization from proliferative diabetic retinopathy; rheumatoid arthritis; bone loss disorders such as osteoporosis, Paget's disease, humoral hypercalcemia of malignancy, hypercalcemia from tumors metastatic to bone, and osteoporosis induced by glucocorticoid treatment; coronary restenosis; and certain microbial infections including those associated with microbial pathogens selected from adenovirus, hantaviruses, *Borrelia burgdorferi, Yersinia* spp., *Bordetella pertussis*, and group A *Streptococcus*.

This invention also relates to a method of (and to a pharmaceutical composition for) treating abnormal cell growth in a mammal which comprise an amount of a compound of formula 1, or a pharmaceutically acceptable salt, solvate or prodrug thereof, and an amount of one or more substances selected from anti-angiogenesis agents, signal transduction inhibitors, and antiproliferative agents, which amounts are together effective in treating said abnormal cell growth.

Anti-angiogenesis agents, such as MMP-2 (matrix-metalloprotienase 2) inhibitors, MMP-9 (matrix-metalloprotienase 9) inhibitors, and COX-II (cyclooxygenase II) inhibitors, can be used in conjunction with a compound of formula 1 in the methods and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 331, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are herein incorporated by reference in their entirety. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in combination with the compounds of the present invention are AG-3340, RO 32-3555, RS 13-0830, and the compounds recited in the following list:

3-[[4-(4-fluoro-phenoxy)-benzenesulfonyl]-(1-hydroxycarbamoyl-cyclopentyl)-amino]-propionic acid;

3-exo-3-[4-(4-fluoro-phenoxy)-benzenesulfonylamino]-8-oxa-bicyclo[3.2.1]octane-3-carboxylic acid hydroxyamide;

(2R,3R)1-[4-(2-chloro-4-fluoro-benzyloxy)-benzenesulfonyl]-3-hydroxy-3-methyl-piperidine-2-carboxylic acid hydroxyamide;

4-[4-(4-fluoro-phenoxy)-benzenesulfonylamino]-tetrahydro-pyran-4-carboxylic acid hydroxyamide;

3-[[4-(4-fluoro-phenoxy)-benzenesulfonyl]-(1-hydroxycarbamoyl-cyclobutyl)-amino]-propionic acid;

4-[4-(4-chloro-phenoxy)-benzenesulfonylamino]-tetrahydro-pyran-4-carboxylic acid hydroxyamide;

3-[4-(4-chloro-phenoxy)-benzenesulfonylamino]-tetrahydro-pyran-3-carboxylic acid hydroxyamide;

(2R,3R)1-[4-(4-fluoro-2-methyl-benzyloxy)-benzenesulfonyl]-3-hydroxy-3-methyl-piperidine-2-carboxylic acid hydroxyamide;

3-[[4-(4-fluoro-phenoxy)-benzenesulfonyl]-(1-hydroxycarbamoyl-1-methyl-ethyl)-amino]-propionic acid;

3-[[4-(4-fluoro-phenoxy)-benzenesulfonyl]-(4-hydroxycarbamoyl-tetrahydro-pyran-4-yl)-amino]-propionic acid;

3-exo-3-[4-(4-chloro-phenoxy)-benzenesulfonylamino]-8-oxa-bicyclo[3.2.1]octane-3-carboxylic acid hydroxyamide;

3-endo-3-[4-(4-fluoro-phenoxy)-benzenesulfonylamino]-8-oxa-bicyclo[3.2.1]octane-3-carboxylic acid hydroxyamide; and 3-[4-(4-fluoro-phenoxy)-benzenesulfonylamino]-tetrahydro-furan-3-carboxylic acid hydroxyamide;

and pharmaceutically acceptable salts, solvates and prodrugs of said compounds.

The compounds of formula 1, and the pharmaceutically acceptable salts, solvates and prodrugs thereof, can also be used in combination with signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor, for example, HERCEPTIN™ (Genentech, Inc. of South San Francisco, Calif., USA).

EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998). EGFR-inhibiting agents include, but are not limited to, the monoclonal antibodies C225 and anti-EGFR 22Mab (ImClone Systems Incorporated of New York, N.Y., USA), the compounds ZD-1839 (AstraZeneca), BIBX-1382 (Boehringer Ingelheim), MDX-447 (Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Mass.).

VEGF inhibitors, for example SU-5416 and SU6668 (Sugen Inc. of South San Francisco, Calif., USA), can also be combined with a compound of formula 1. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are herein incorporated by reference in their entirety. Other examples of some specific VEGF inhibitors are IM862 (Cytran Inc. of Kirkland, Wash., USA); anti-VEGF monoclonal antibody of Genentech, Inc. of South San Francisco, Calif.; and angiozyme, a synthetic ribozyme from Ribozyme (Boulder, Colo.) and Chiron (Emeryville, Calif.).

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), may be administered in combination with a compound of formula 1. Such erbB2 inhibitors include those described in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), each of which is herein incorporated by reference in its entirety. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are herein incorporated by reference in their entirety.

Other antiproliferative agents that may be used with the compounds of the present invention include inhibitors of the enzyme farnesyl protein transferase and inhibitors of the receptor tyrosine kinase PDGFr, including the compounds disclosed and claimed in the following U.S. patent application Ser. No. 09/221946 (filed Dec. 28, 1998); Ser. No. 09/454058 (filed Dec. 2, 1999); Ser. No. 09/501163 (filed Feb. 9, 2000); Ser. No. 09/539930 (filed Mar. 31, 2000); Ser. No. 09/202796 (filed May 22, 1997); Ser. No. 09/384339 (filed Aug. 26, 1999); and Ser. No. 09/383755 (filed Aug. 26, 1999); and the compounds disclosed and claimed in the following U.S. provisional patent applications: 60/168207 (filed Nov. 30, 1999); 60/170119 (filed Dec. 10, 1999); 60/177718 (filed Jan. 21, 2000); 60/168217 (filed Nov. 30, 1999), and 60/200834 (filed May 1, 2000). Each of the foregoing patent applications and provisional patent applications is herein incorporated by reference in their entirety.

A compound of formula 1 may also be used with other agents useful in treating abnormal cell growth or cancer, including, but not limited to, agents capable of enhancing antitumor immune responses, such as CTLA4 (cytotoxic lymphocyte antigen 4) antibodies, and other agents capable of blocking CTLA4; and anti-proliferative agents such as other farnesyl protein transferase inhibitors, for example the farnesyl protein transferase inhibitors described in the references cited in the "Background" section, supra. Specific CTLA4 antibodies that can be used in the present invention include those described in U.S. Provisional Application 60/113,647 (filed Dec. 23, 1998) which is herein incorporated by reference in its entirety.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

BRIEF DESCRIPTION OF THE DRAWINGS

FIG. 3A shows a powder X-ray diffraction pattern of a maleate salt of 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide, including polymorph Form 3 in a polymorph mixture.

FIG. 10A shows a dynamic moisture sorption gravimetry (DMSG) scan for a first hydrochloride salt of 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide.

DETAILED DESCRIPTION OF THE INVENTION

Figure 1:
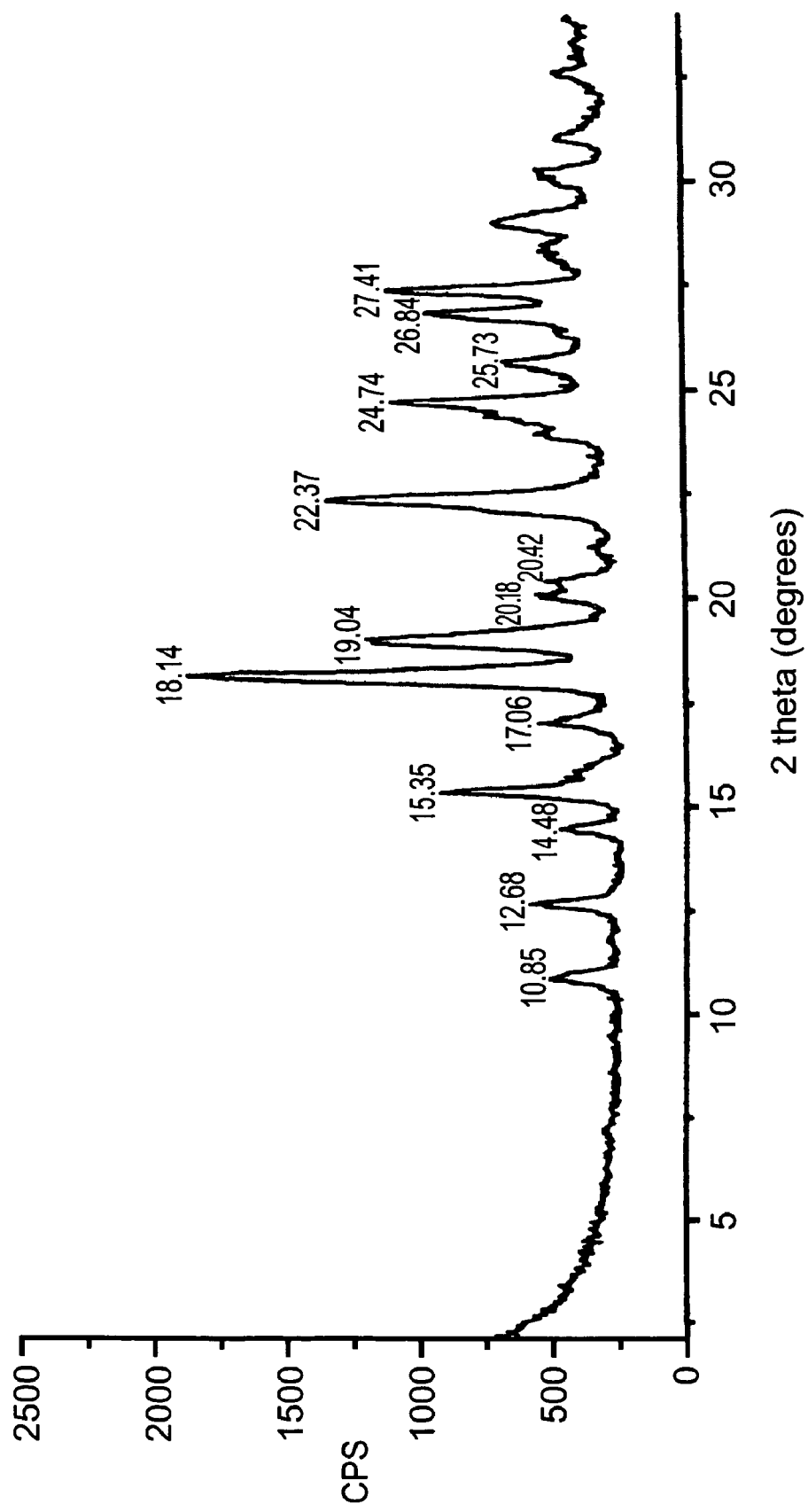
FIG. 1 shows a powder X-ray diffraction pattern of a maleate salt of 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide, polymorph Form 1.

The compound 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide can be prepared according to methods described in U.S. Pat. No. 6,573,293 and U.S. patent application publication No. 2003/0092917, published May 15, 2003, the entire disclosures of which are incorporated herein by reference.

Salts of 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide are readily prepared by treating the free base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

The maleate salt of 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide can be produced with good crystallinity using, for example, room temperature evaporation in ethanol or acetonitrile/water (1:1), heat evaporation in methanol/ethyl acetate, drowning in ethanol/hexane, room temperature slow evaporation in isopropanol, or room temperature slurry in acetonitrile or isopropanol, to name but a few acceptable methods and solvent systems. It was observed that samples of fair or poor crystallinity were produced using room temperature evaporation in water, acetonitrile, isopropanol, isopropanol/water (1:1) and methanol; room temperature slurry in acetonitrile and isopropanol; and drowning in ethanol/hexane.

The hydrochloride salt of 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide can be produced with good crystallinity by distillation from acetonitrile/ethanol/water.

Seven polymorph forms of the maleate salt of 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide have been identified and characterized. PXRD patterns for these forms, denoted Forms 1 through 7, are shown in FIGS. 1 through 7.

Polymorph Form 1 can be produced by cooling from 80° C. to 5° C. in cyclopentanone or nitrobenzene. The infrared spectrum (600 cm$^{-1}$ to 4000 cm$^{-1}$) of polymorph Form 1 (peak table) is shown in Table 3, and the PXRD pattern in FIG. 1. Analysis by DSC and TGA show that this form melts with a peak melting point of 220° C. and onset melting point of 215° C.; as the sample melts, a simultaneous TGA weight loss occurs. Full decomposition starts at 315° C.

TABLE 3

Form 1, Infrared Peaks

| λ (cm$^{-1}$) | Transmittance (%) |
|---|---|
| 3314.7 | 31 |
| 3158.4 | 42 |
| 3119.9 | 49 |
| 3099.6 | 50 |
| 3056.2 | 54 |
| 3024.4 | 54 |
| 2954.0 | 4 |
| 2924.1 | 1 |
| 2869.1 | 10 |
| 2854.6 | 5 |
| 2768.8 | 71 |
| 2725.4 | 72 |
| 2706.1 | 71 |
| 2641.5 | 73 |
| 2415.8 | 72 |
| 1996.3 | 76 |
| 1835.3 | 79 |
| 1724.4 | 80 |
| 1684.8 | 63 |
| 1657.8 | 10 |
| 1630.8 | 9 |
| 1602.8 | 34 |
| 1570.1 | 11 |
| 1556.6 | 4 |
| 1498.7 | 19 |
| 1479.4 | 6 |
| 1465.9 | 14 |
| 1454.3 | 10 |
| 1445.6 | 8 |
| 1412.9 | 54 |
| 1387.8 | 43 |
| 1377.2 | 37 |
| 1359.8 | 25 |
| 1323.2 | 6 |
| 1302.9 | 36 |
| 1294.2 | 47 |
| 1280.7 | 27 |
| 1261.4 | 18 |
| 1235.4 | 30 |
| 1213.2 | 43 |
| 1196.8 | 11 |
| 1169.8 | 38 |
| 1154.4 | 20 |
| 1135.1 | 31 |
| 1112.9 | 53 |

TABLE 3-continued

Form 1, Infrared Peaks

| λ (cm$^{-1}$) | Transmittance (%) |
|---|---|
| 1099.4 | 39 |
| 1077.2 | 51 |
| 1065.7 | 52 |
| 1058.0 | 38 |
| 1037.7 | 37 |
| 1021.3 | 70 |
| 1002.0 | 79 |
| 979.8 | 57 |
| 956.7 | 83 |
| 935.5 | 76 |
| 922.9 | 69 |
| 917.1 | 70 |
| 902.7 | 83 |
| 887.3 | 74 |
| 878.6 | 73 |
| 866.0 | 23 |
| 808.2 | 35 |
| 800.5 | 42 |
| 780.2 | 53 |
| 773.5 | 53 |
| 759.0 | 70 |
| 731.0 | 67 |
| 725.2 | 72 |
| 698.2 | 76 |
| 668.3 | 23 |
| 650.0 | 62 |
| 626.9 | 61 |
| 605.6 | 57 |

Polymorph Form 2 can be produced by cooling from 80° C. to 5° C. preferably in a polar solvent, preferably cooled slowly (e.g., 0.6° C./min), and preferably using a long aging time (e.g., 48 hours). The infrared spectrum (600 cm$^{-1}$ to 4000 cm$^{-1}$) of polymorph Form 2 (peak table) is shown in Table 4, and the PXRD pattern in FIG. 2. Analysis by DSC and TGA show that this form melts with a peak melting point of 224° C. and onset melting point of 221° C.

TABLE 4

Form 2, Infrared Peaks

| λ (cm$^{-1}$) | Transmittance (%) |
|---|---|
| 3313.7 | 34 |
| 3171.0 | 41 |
| 3119.9 | 48 |
| 3053.3 | 51 |
| 3023.4 | 51 |
| 2954.9 | 11 |
| 2925.0 | 5 |
| 2869.1 | 18 |
| 2854.6 | 13 |
| 2806.4 | 62 |
| 2704.2 | 68 |
| 2641.5 | 69 |
| 2416.8 | 69 |
| 1835.3 | 78 |
| 1824.7 | 80 |
| 1685.8 | 62 |
| 1657.8 | 20 |
| 1630.8 | 18 |
| 1574.9 | 21 |
| 1556.6 | 11 |
| 1497.7 | 25 |
| 1480.4 | 15 |
| 1464.0 | 19 |
| 1454.3 | 16 |
| 1445.6 | 16 |

TABLE 4-continued

Form 2, Infrared Peaks

| λ (cm$^{-1}$) | Transmittance (%) |
|---|---|
| 1428.3 | 40 |
| 1412.9 | 52 |
| 1386.8 | 43 |
| 1377.2 | 40 |
| 1359.8 | 32 |
| 1322.2 | 14 |
| 1302.9 | 39 |
| 1294.2 | 46 |
| 1278.8 | 33 |
| 1260.5 | 24 |
| 1234.4 | 35 |
| 1213.2 | 45 |
| 1196.8 | 20 |
| 1168.9 | 40 |
| 1157.3 | 31 |
| 1135.1 | 34 |
| 1112.0 | 51 |
| 1098.5 | 40 |
| 1095.6 | 41 |
| 1077.2 | 48 |
| 1065.7 | 51 |
| 1058.0 | 40 |
| 1037.7 | 39 |
| 1021.3 | 63 |
| 979.8 | 54 |
| 955.7 | 79 |
| 935.5 | 72 |
| 925.8 | 71 |
| 921.0 | 70 |
| 913.3 | 65 |
| 902.7 | 80 |
| 887.3 | 72 |
| 877.6 | 71 |
| 865.1 | 28 |
| 813.0 | 43 |
| 807.2 | 43 |
| 780.2 | 55 |
| 773.5 | 55 |
| 749.3 | 70 |
| 731.0 | 64 |
| 724.3 | 68 |
| 698.2 | 74 |
| 668.3 | 31 |
| 651.0 | 62 |
| 629.6 | 63 |
| 606.6 | 62 |

Mixtures of polymorph forms 1 and 2 can be produced in ethanol and THF/water solvents.

Figure 3B:
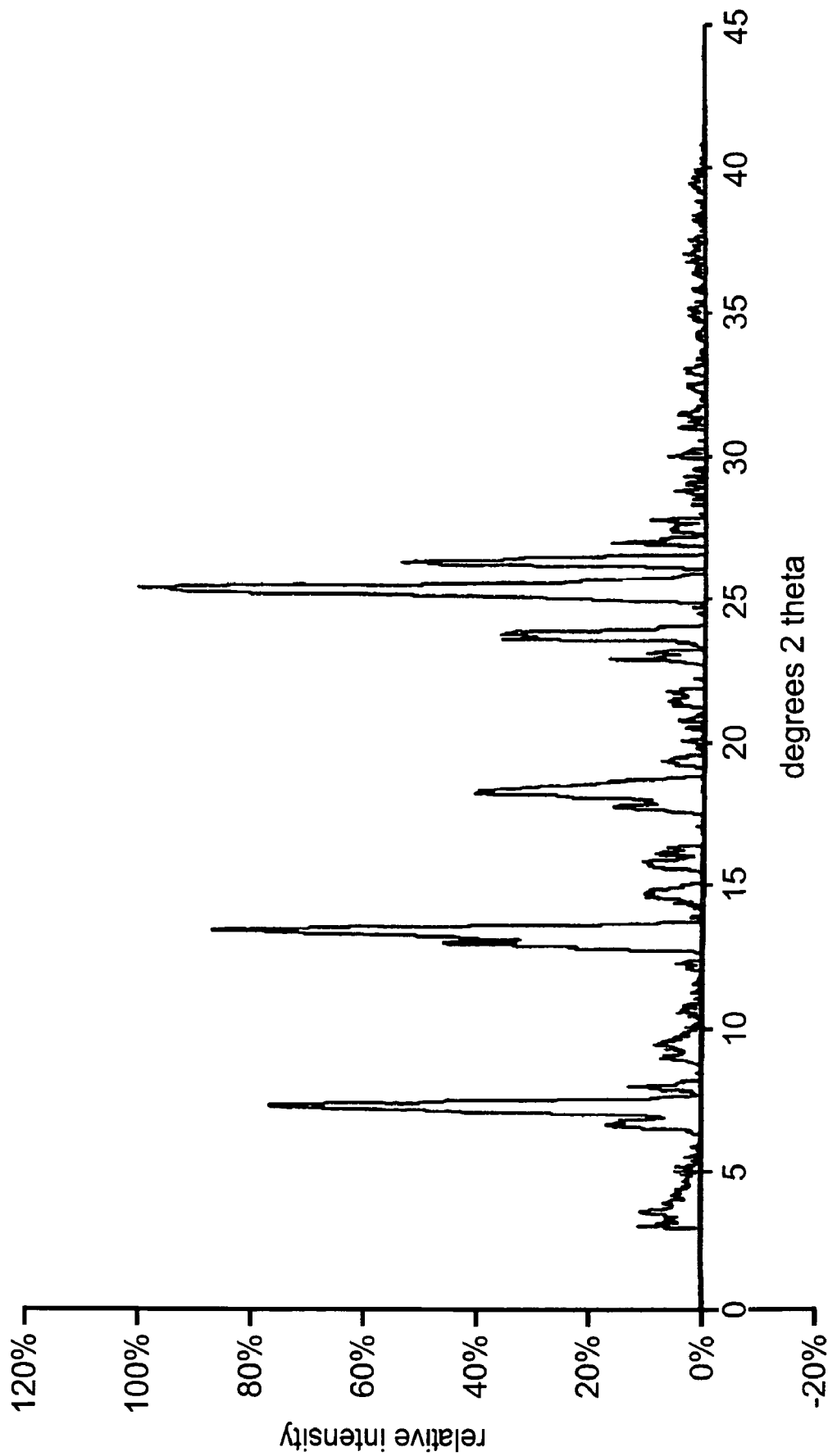
FIG. 3B shows a deconvoluted powder X-ray diffraction pattern of a maleate salt of 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide, polymorph Form 3.
Figure 4:
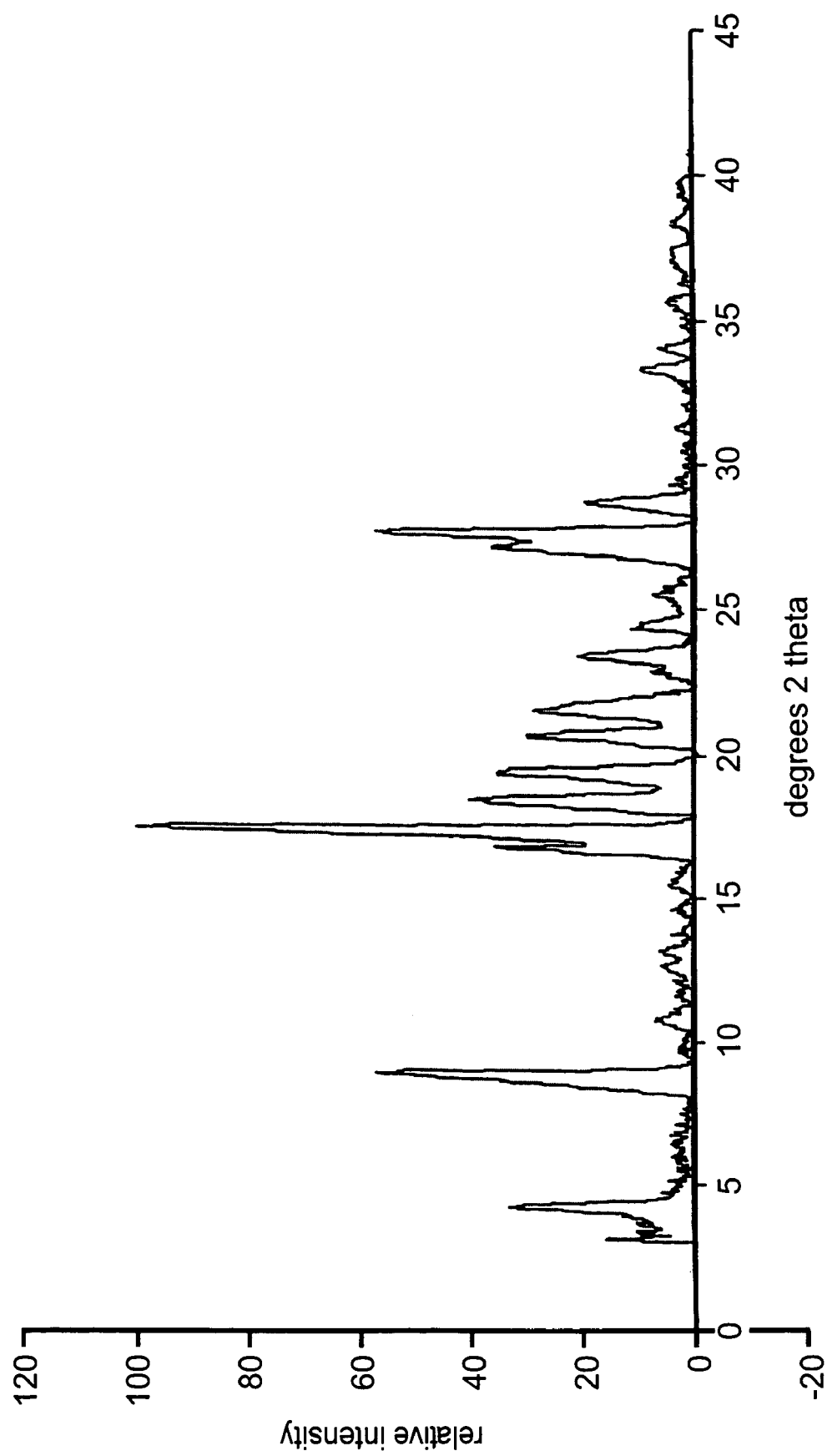
FIG. 4 shows a powder X-ray diffraction pattern of a maleate salt of 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide, polymorph Form 4.
Figure 5:
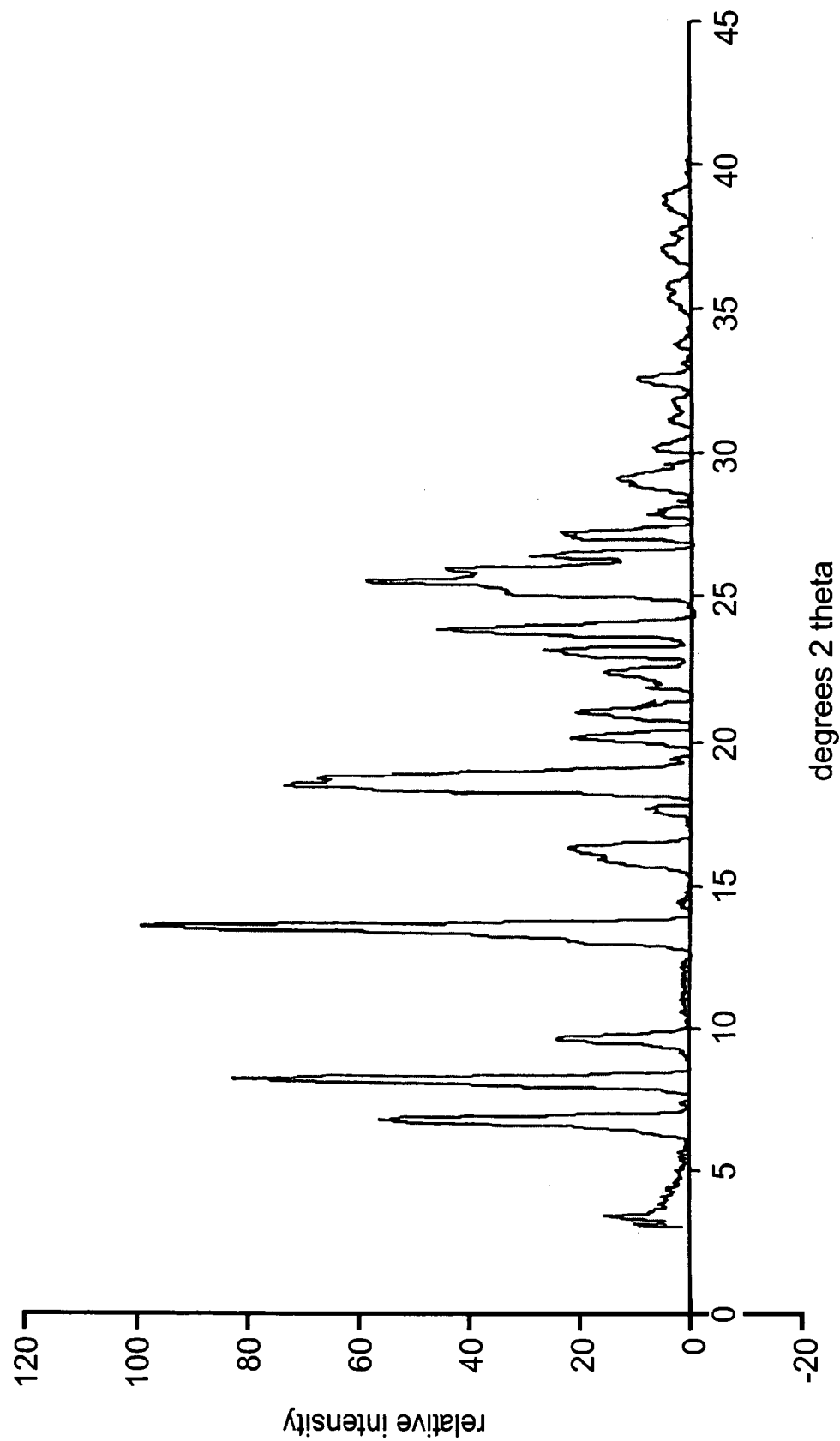
FIG. 5 shows a powder X-ray diffraction pattern of a maleate salt of 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide, polymorph Form 5.

Polymorph Form 3 can be produced by cooling from 80° C. to 5° C. in water. Attempts to produce polymorph form 3 resulted in mixtures with forms 2 or 5. FIG. 3A shows a typical PXRD pattern, and FIG. 3B shows the pattern deconvoluted to show a calculated pure polymorph Form 3 pattern. Polymorph Form 3 may be a hydrate; however, this was not confirmed.

Polymorph Form 4 can be produced by cooling from 80° C. to 5° C. in 4-methyl morpholine or triethylamine.

Polymorph Form 5 can be produced by cooling from 80° C. to 5° C. preferably in a polar solvents, preferably at a rapid cooling rate (e.g., 300° C./min) and short aging time (e.g., 1 hour). Polymorph Form 6 can be produced by cooling from 80° C. to 5° C. in a variety of solvents including esters, ketones, alcohols, alkanes and amines, preferably using a rapid cooling rate (e.g., 300° C./min) and a short aging time (e.g., 1 hour). Attempts to produce polymorph Form 6 resulted in mixtures with forms 2 or 5.

Figure 6A:
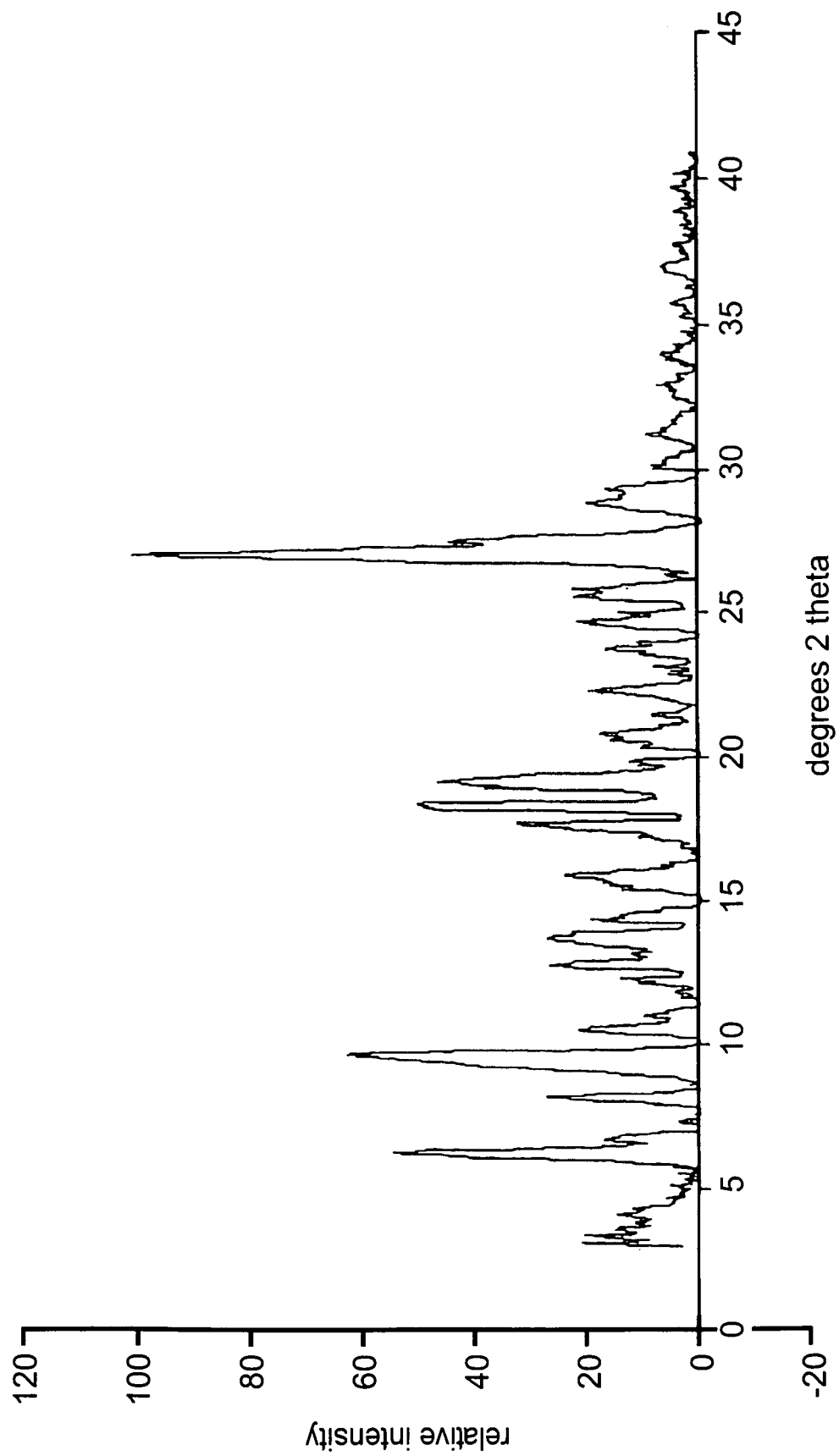
FIG. 6A shows a powder X-ray diffraction pattern of a maleate salt of 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide, including polymorph Form 6 in a polymorph mixture.
Figure 6B:
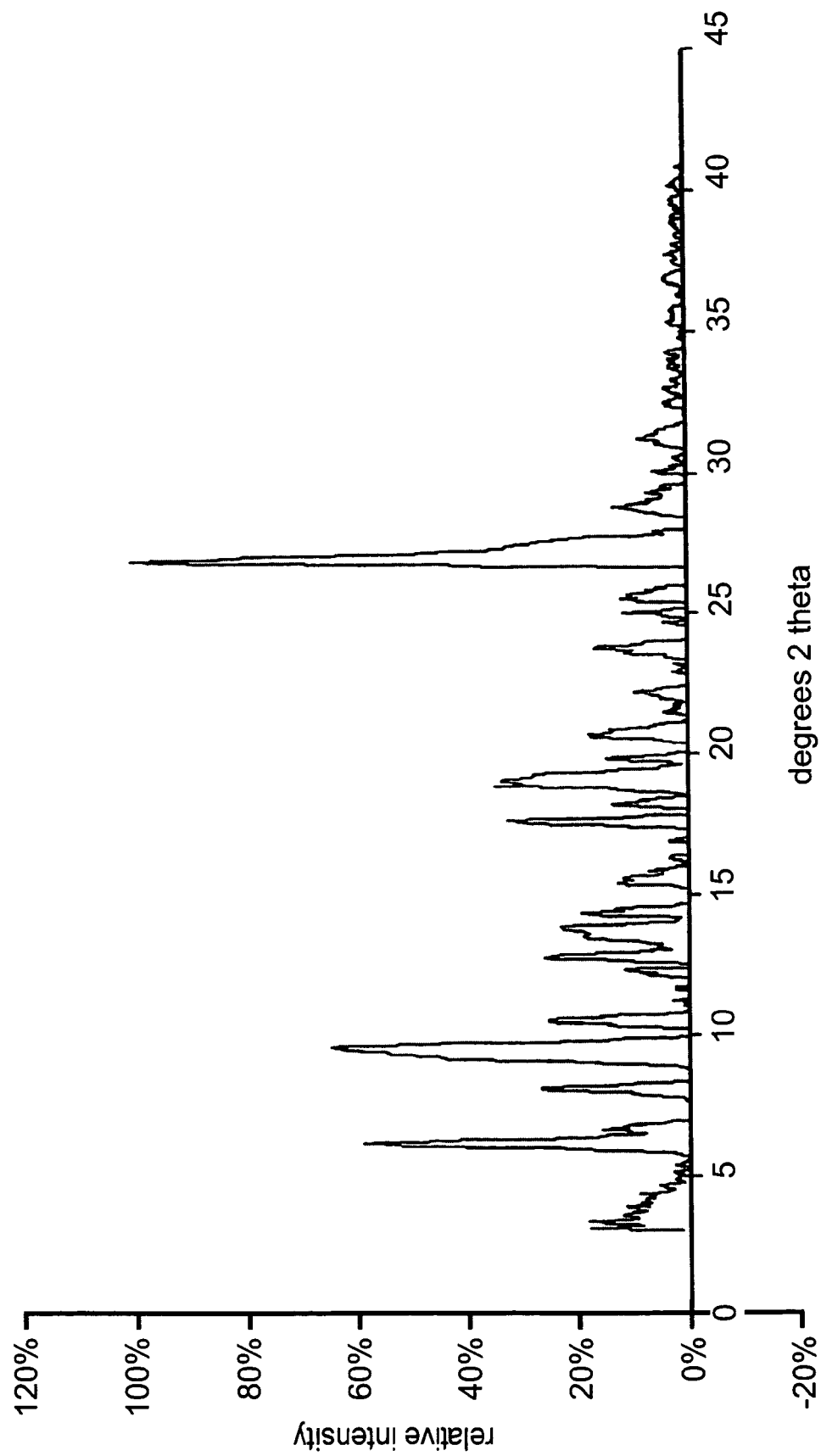
FIG. 6B shows a deconvoluted powder X-ray diffraction pattern of a maleate salt of 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide, polymorph Form 6.
Figure 7:
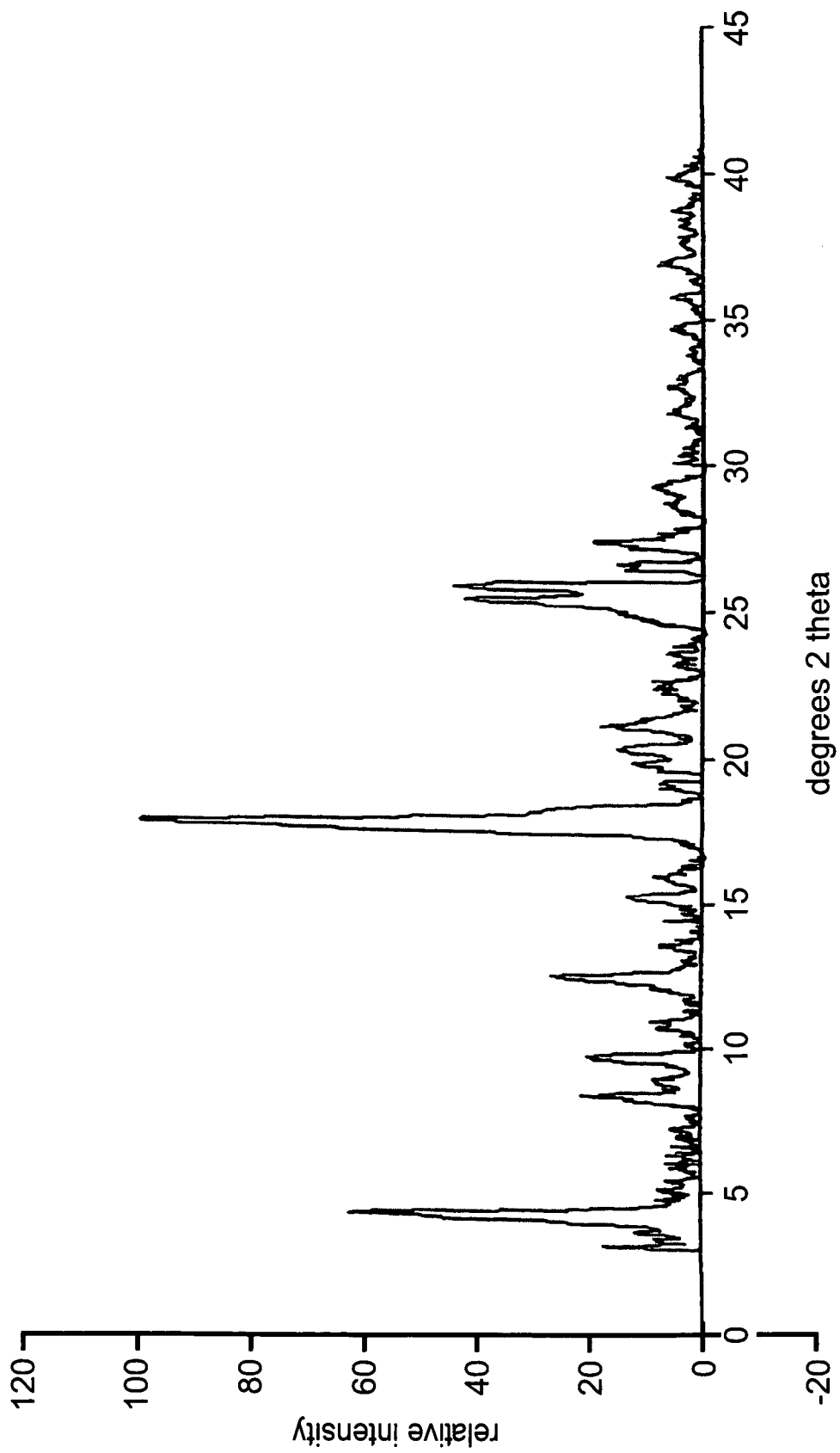
FIG. 7 shows a powder X-ray diffraction pattern of a maleate salt of 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide, polymorph Form 7.

FIG. 6A shows a typical PXRD pattern, and FIG. 6B shows the pattern deconvoluted to show a calculated pure polymorph Form 6 pattern.

Polymorph Form 7 can be produced by cooling from 80° C. to 5° C. in propan-1,2-diol. Polymorph form 7 may be a solvate; however, this was not confirmed.

Polymorph forms 3–7 are not stable, and convert over time to polymorph Form 2.

Pharmaceutical compositions of the invention may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Preferred methods of formulating pharmaceutical compositions of the invention are described in U.S. provisional patent application No. 60/421,133, filed Sep. 10, 2002, the disclosure of which is incorporated herein by reference in its entirety.

Methods of preparing various pharmaceutical compositions with a specific amount of active compound are known, or will be apparent, to those skilled in this art. For examples, see *Remington's Pharmaceutical Sciences*, Mack Publishing Company, Easter, Pa., 15th Edition (1975).

EXAMPLES

The examples and preparations provided below further illustrate and exemplify particular aspects of embodiments of the invention. It is to be understood that the scope of the present invention is not limited in any way by the scope of the following examples.

Methods and Materials

Differential Scanning Calorimetry (DSC): DSC measurements were performed with a TA Instruments model 2920 differential scanning calorimeter with a Thermal Analyst 5000 controller. Samples ranged in weight from 0.4 to 2 mg. The samples were placed in crimped aluminum pans and heated at a rate of 10° C./min up to 320° C. Dry nitrogen was used as a purge gas.

Powder X-ray Diffraction (PXRD): PXRD data for FIGS. 1 and 2, and in the following examples, were collected using either a Scintag X2 or X1 Advanced Diffraction System. The system used a copper X-ray source maintained at 45 kV and 40 mA to provide CuKα1 emission at 1.5406 Å (0.15406 nm), and a solid state peltier cooled detector. Beam aperture was controlled using tube divergence and antiscatter slits of 2 and 4 mm, and detector antiscatter and receiving slits of 0.5 and 0.3 mm width. Data were normally collected from 2° to 40° two-theta (2θ) using a step scan of 0.03°/point and a 1 s/point count time. Scintag, round top loading stainless steel sample cups with a 12 mm or 9 mm aluminum tray insert or a quartz plate were used to contain samples. As necessary, samples were hand ground with a mortar and pestle before analysis. The intensity data in Tables 1 and 2 were roughly corrected for background by subtracting the approximate background counts per second from each point.

PXRD data for FIGS. 3-9 were collected using a high-throughput PXRD screening apparatus. Plates were mounted on a Bruker GADDS diffractometer equipped with a Hi-Star area detector. The data collection was carried out at room temperature using monochromated CuKα radiation in the region of 2θ from 3 to 42°. The diffraction pattern of each well was collected in two theta ranges (3≦2θ≦21° for the first frame and 19≦2θ≦42° for the second frame) with an exposure time of 75 s for each frame. The carrier material used during PXRD analysis was transparent to X-rays and contributed only slightly to the background.

TGA measurements were performed using a TA Instruments model 2950 Hi-Res analyzer with a Thermal Analyst 5000 controller. Samples were placed onto a tared platinum hanging pan and heated to at least 165° C. at a rate of 10° C./min. Dry nitrogen was used as a purge gas.

HPLC conditions are given in the individual examples.

Example 1

Several salts of 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide were produced and analyzed for hygroscopicity. Hygroscopicity was determined by dynamic moisture sorption gravimetry (DMSG) using a controlled atmosphere microbalance at a temperature of 25° C. Samples were analyzed over a relative humidity range of from 0 to 90% in 3% steps, in a humidity profile of 36→0→9→0%, where the initial value of 36% reflects the approximate initial equilibrated relative humidity (not specifically measured). Each step was brought to equilibrium before moving to the next step, with equilibrium assessed as a weight change of less than 0.001 mg (0.01%) or 0.002 mg (0.02%) for five consecutive points at 1 point per 120 seconds. The water uptake at 80% relative humidity (RH) was selected for comparison between the salts. The 80% RH values for each salt are shown in Table 5, and the right column of the table identifies the corresponding Figure showing the complete DMSG scan. A range of values given for the water uptake at 80% reflects hysteresis in the 0→90% and 90→0% scans.

TABLE 5

| Salt | Water Uptake at 80% RH (wt. %) | FIG. No. |
| --- | --- | --- |
| HCl, form 1 | 3–20 | 10A |
| HCl, form 2 | 1.2 | 10B |
| L-malate | 12–13 | 11 |
| Maleate | 0.8 | 12 |
| L-tartrate | 9 | 13 |
| Tosylate | 7 | 14 |
| Mandalate | 5–6 | 15 |
| Malonate | 12 | 16 |

Figure 10B:
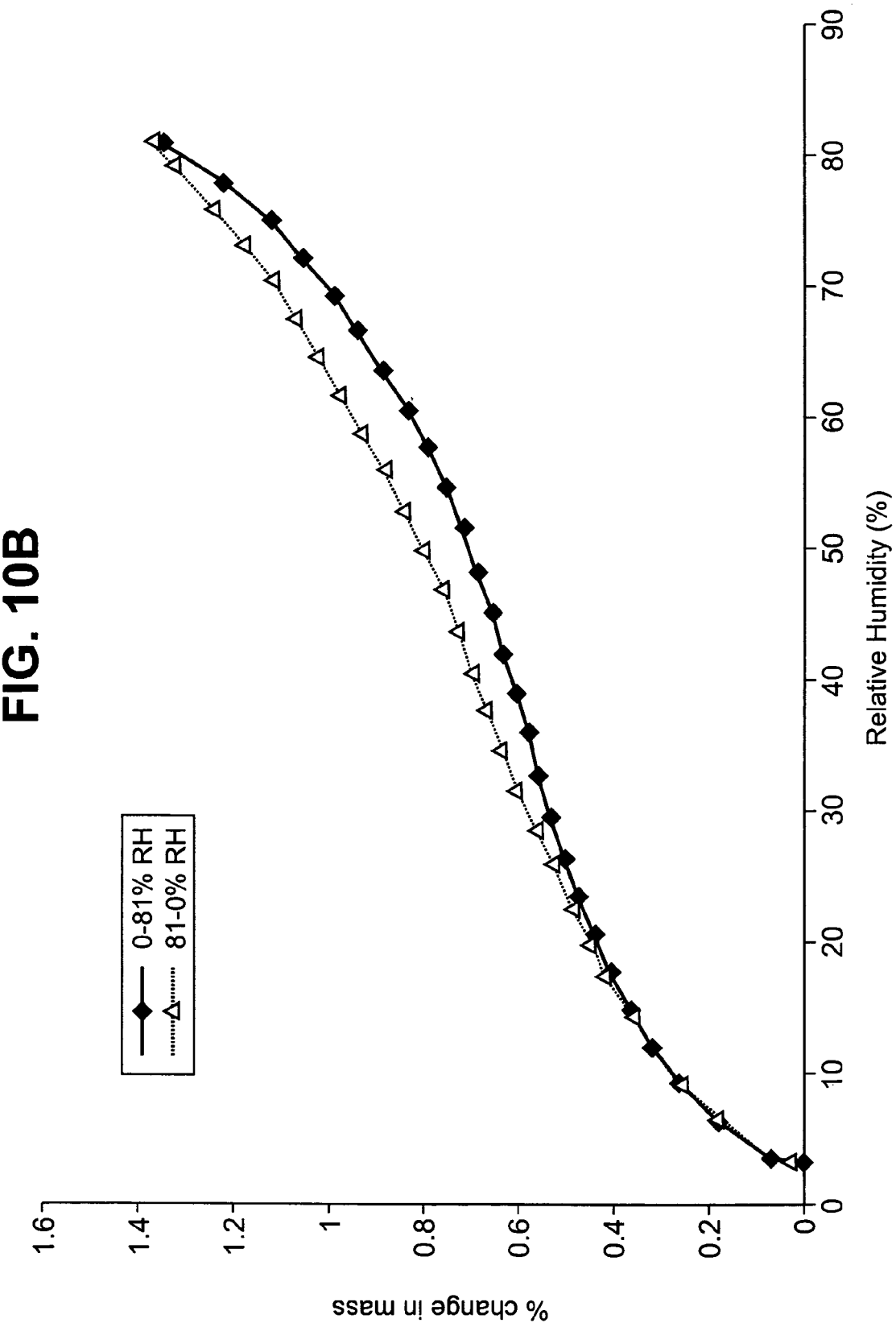
FIG. 10B shows a dynamic moisture sorption gravimetry (DMSG) scan for a second hydrochloride salt of 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide.
Figure 11:
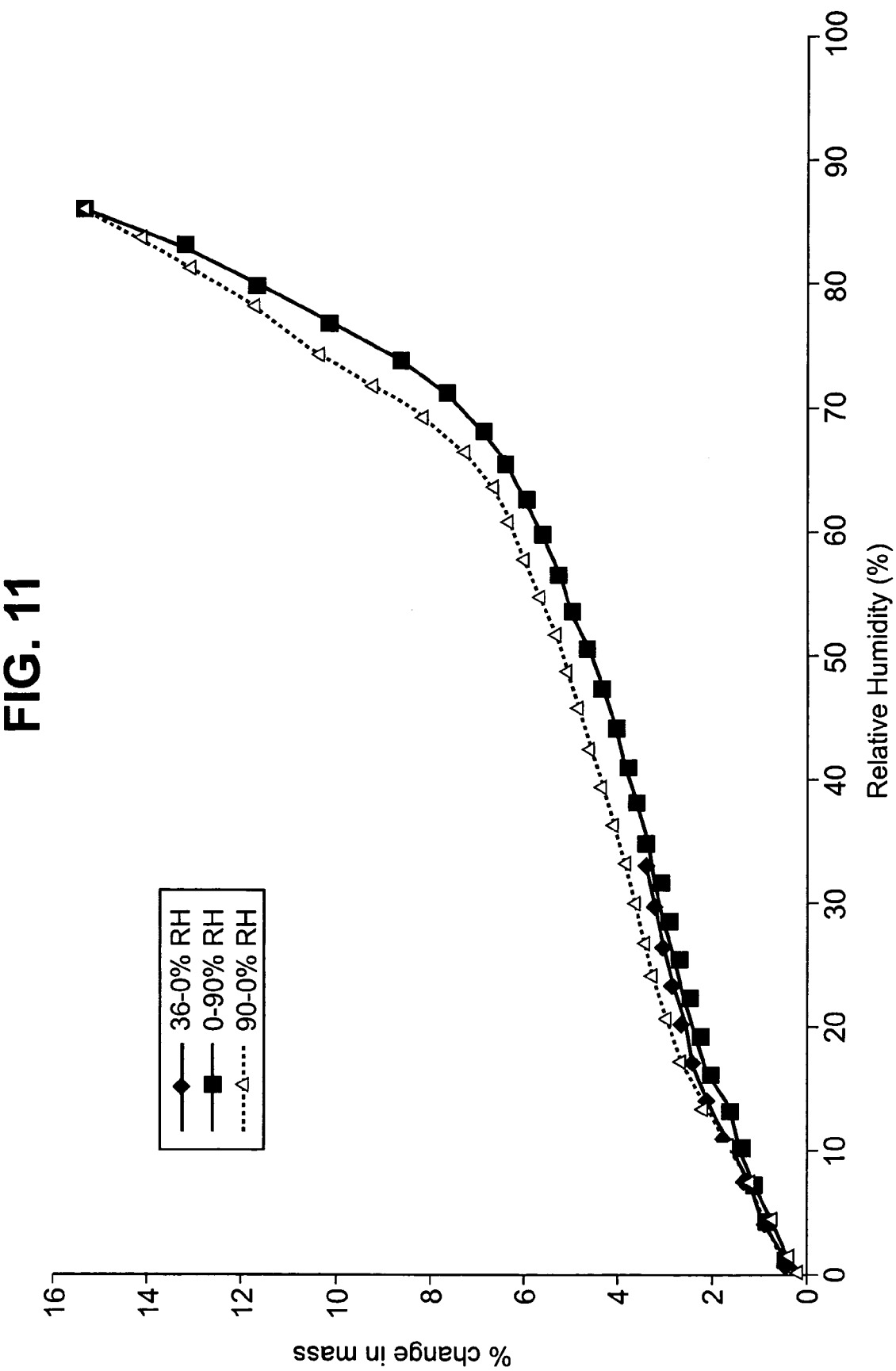
FIG. 11 shows a dynamic moisture sorption gravimetry (DMSG) scan for an L-malate salt of 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide.
Figure 12:
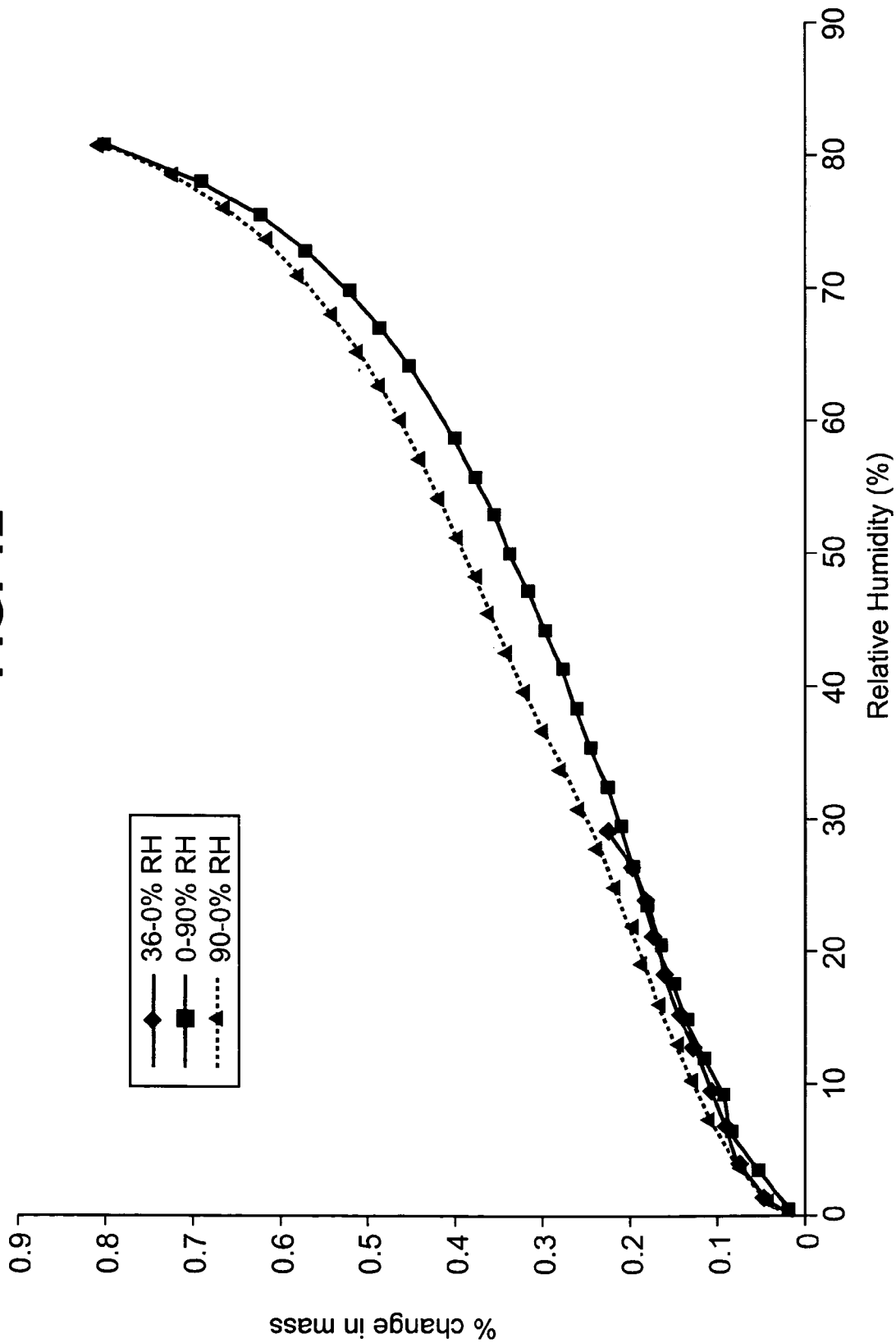
FIG. 12 shows a dynamic moisture sorption gravimetry (DMSG) scan for a maleate salt of 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide.
Figure 13:
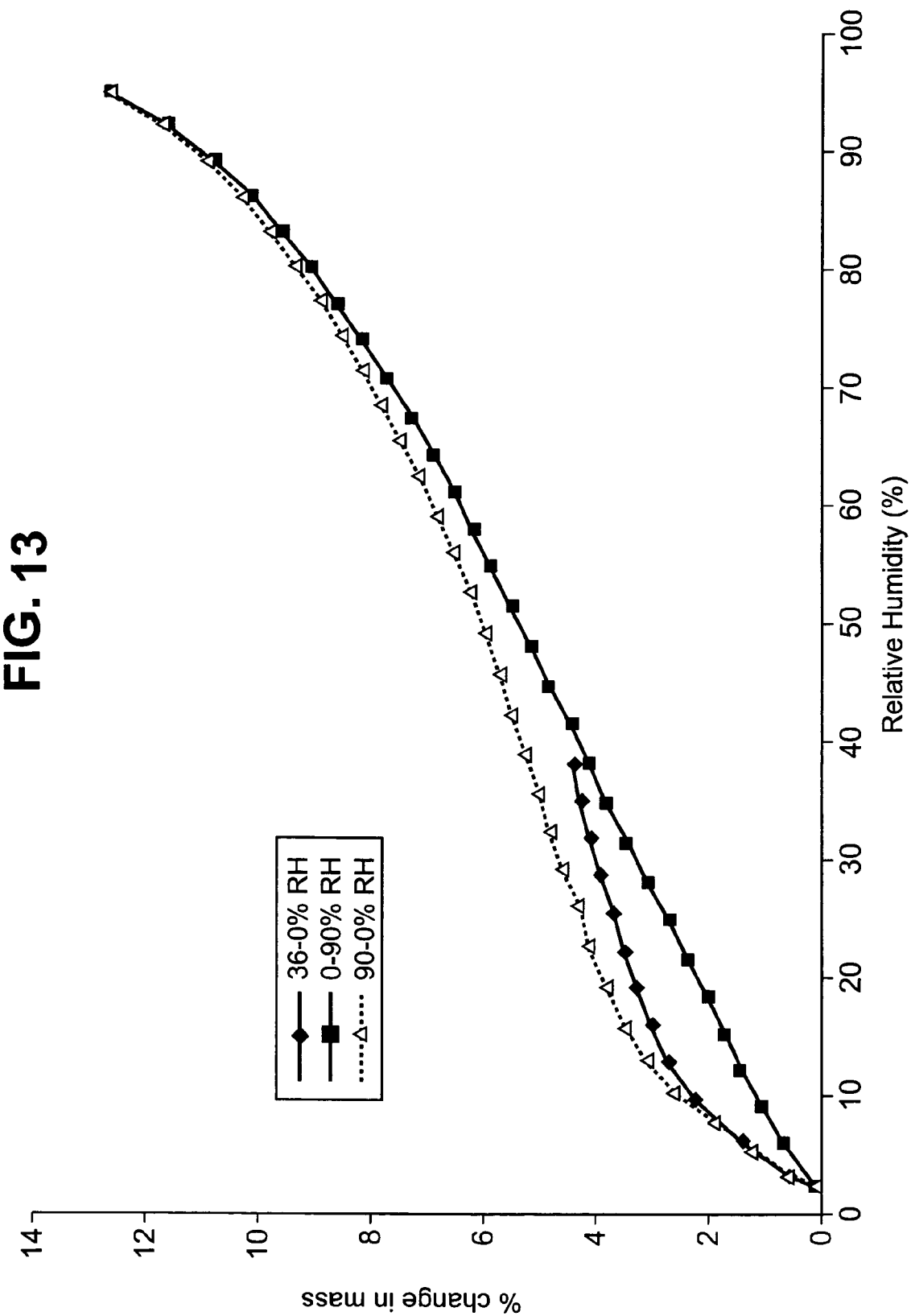
FIG. 13 shows a dynamic moisture sorption gravimetry (DMSG) scan for an L-tartrate salt of 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide.
Figure 14:
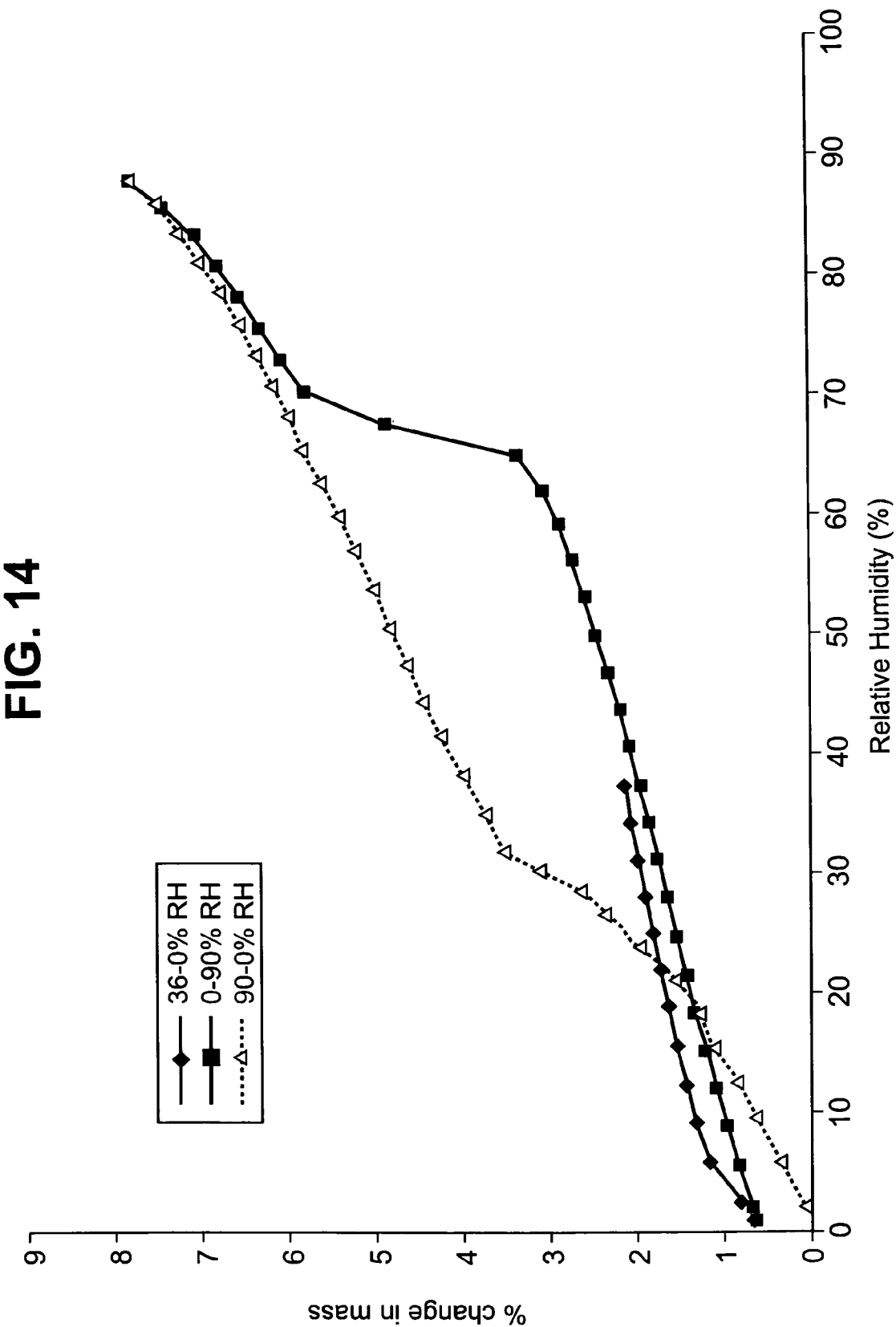
FIG. 14 shows a dynamic moisture sorption gravimetry (DMSG) scan for a tosylate salt of 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide.
Figure 15:
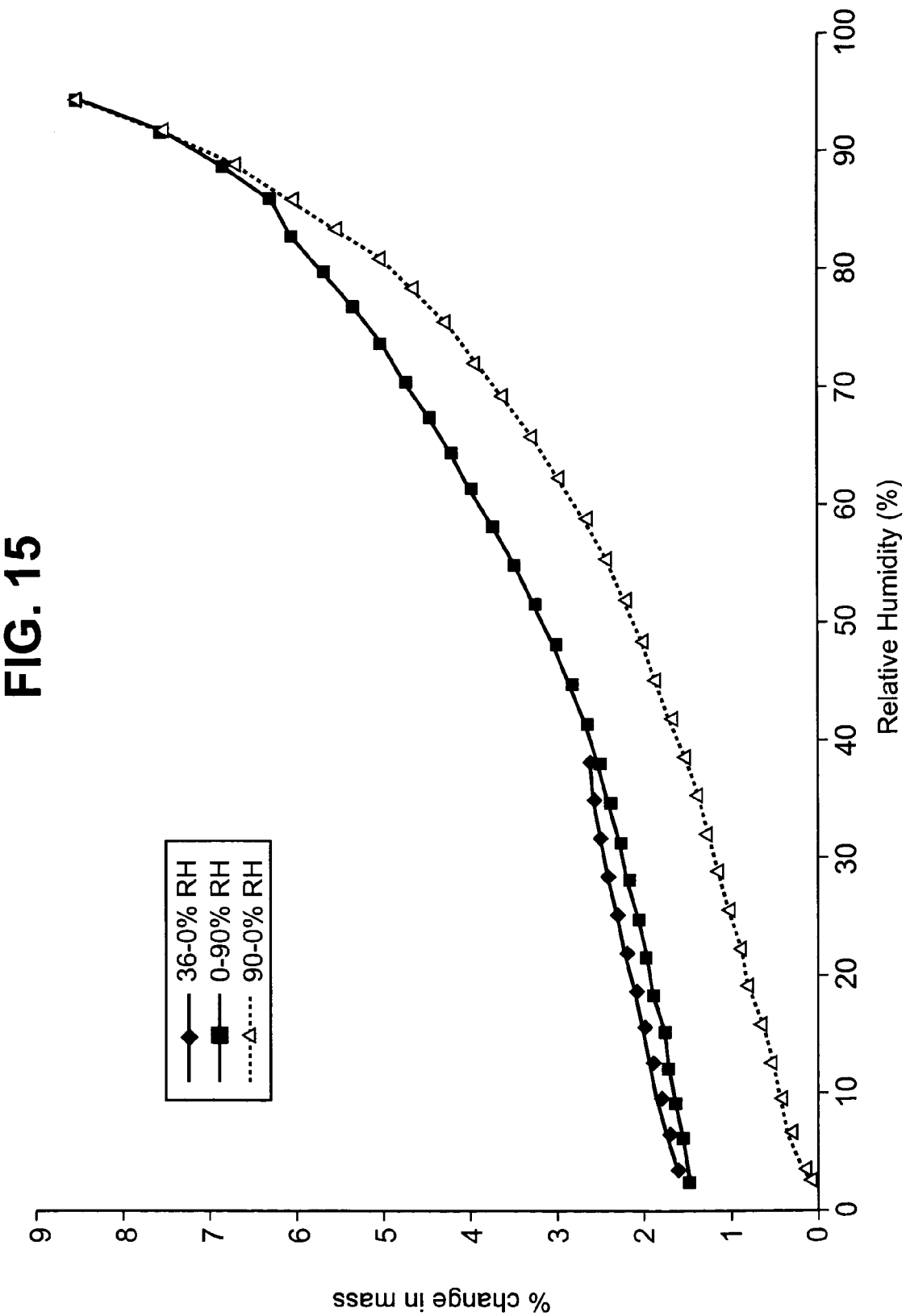
FIG. 15 shows a dynamic moisture sorption gravimetry (DMSG) scan for a mandelate salt of 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide.
Figure 16:
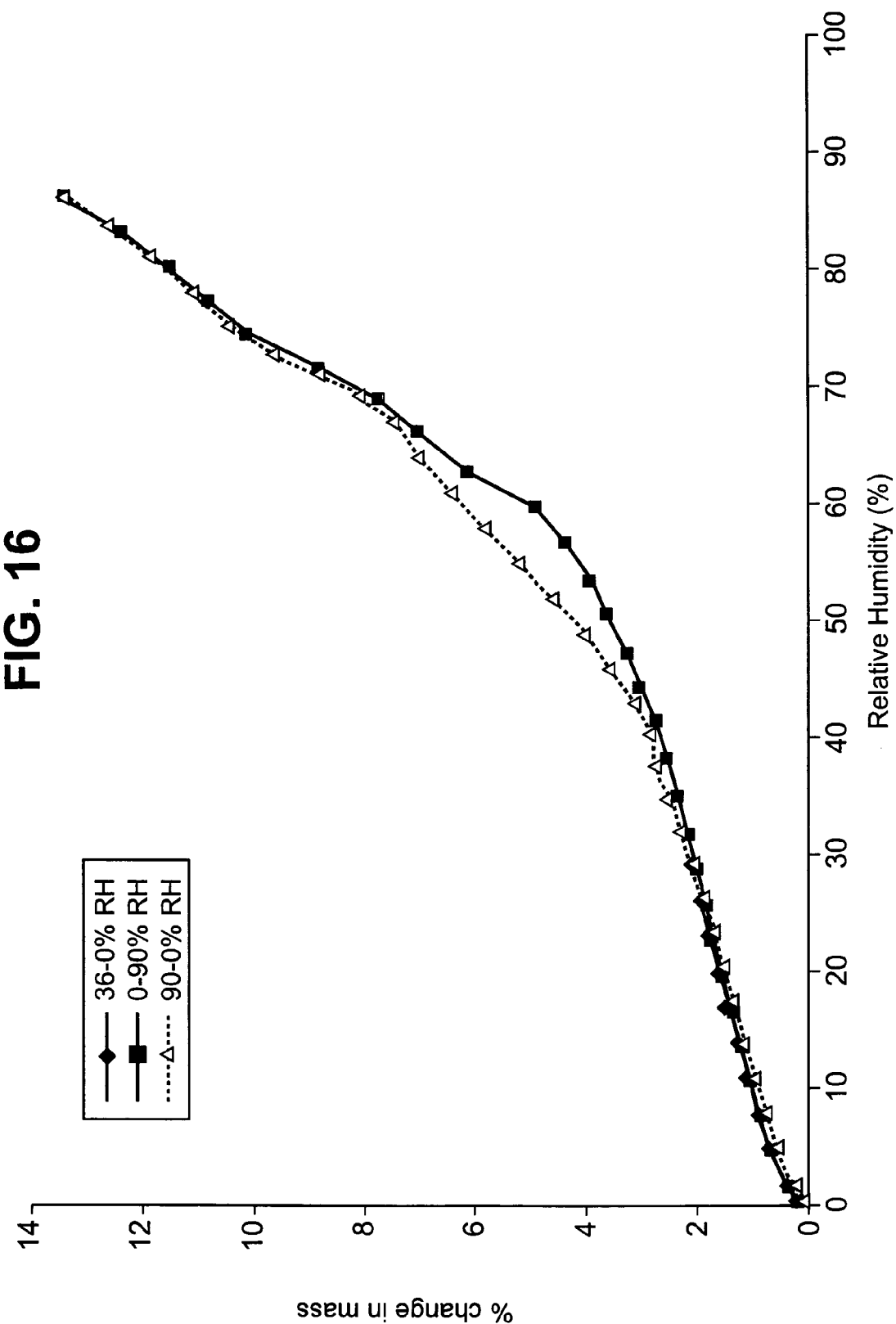
FIG. 16 shows a dynamic moisture sorption gravimetry (DMSG) scan for a malonate salt of 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide.

For the hydrochloride salt, the initial measurement exhibited sorption with an apparent stepwise gain/loss of water; the sorption profile exhibited significant hysteresis (see FIG. 10A). This salt is designated "form 1" in Table 5. The final product (HCl "form 2") was not the same crystal form as the starting material, as evaluated by PXRD (not shown). DSC and TGA measurements on the HCl form 2 salt indicated a monohydrate with a melting point of about 284° C. TGA found 3.8% weight loss. The HCl form 2 salt was also evaluated by DMSG, but using a 0→81→0% relative humidity profile (FIG. 10B). The form 2 salt was relatively non-hygroscopic and showed no significant hysteresis.

The L-malate salt was of poor crystallinity (PXRD not shown). The sample melted at about 182° C.; however, additional thermal events occurred at about 95° C.

Initial data collected using a maleate salt are omitted. The initial maleate salt was only of fair crystallinity, exhibiting a unique PXRD pattern and having a melting point of about 181° C. This material was hygroscopic, having a moisture uptake of about 9% at 80% relative humidity. This salt is believed to be polymorph Form 5 or a mixture of Form 5 with one ore more other polymorphs, but this was not verified. A second maleate salt sample having good crystallinity and characterized as polymorph Form 2 was subsequently tested, and the results from this polymorph Form 2 sample are shown in Table 5.

The L-tartrate salt was of poor crystallinity (PXRD not shown). The sample melted at about 191° C.

The tosylate salt was of fair crystallinity (PXRD not shown). The sample melted at about 190° C. Uptake of about 2.5% water was observed at about 65% relative humidity, with subsequent loss at about 30% relative humidity. This weight change was approximately equal to 1 mole of water.

The mandelate salt was of poor crystallinity (PXRD not shown). The sample melted at about 224° C.

The malonate salt was of poor crystallinity (PXRD not shown). The sample desolvated (DSC) at about 133° C. and melted at about 261° C. Solvent content of about 15% was determined by TGA.

Example 2

Chemical stability was assessed for two different samples of 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide maleate salt, polymorph Form 1. Samples were maintained in a temperature and humidity-controlled chamber at 25° C. and 60% relative humidity (Tables 7 and 8) or at 40° C. and 75% relative humidity (Tables 9 and 10). At various time intervals, material was removed and tested for maleate counterion assay, impurities, water content and enantiomeric purity.

The maleate counterion assay was determined by ion exchange chromatography (IEC).

Typical conditions were as follows:
  Ionic Chromatograph: Dionex DX 600 with conductivity detector
  Analytical Column: Anionic AS14, 250×4.0 mm, Dionex
  Guard Column: Anionic AS14, 100×4.0 mm, Dionex
  Column Temperature: 30° C.
  Mobile Phase: 3.5 mM sodium carbonate plus 1 mM sodium hydrogen carbonate
  Elution Mode: isocratic
  Flow Rate: 1.2 mL/min
  Injection Volume: 25 μL A suitable amount of the maleate salt is dissolved in water (Milli Q grade) and analyzed by IEC, and compared to calibration samples. Under these conditions, the peak due to maleic acid has a retention time of about 11 minutes. The amount of maleic acid in the sample is calculated as:

% Assay=$(C_s/W) \times 100$ where $C_s$ is the concentration of maleic acid found in the sample, and W is the theoretical sample concentration in the aqueous solution.

The amounts of impurities and degradation products were determined by HPLC, using a Perkin Elmer LC 200 system with a diode array detector. The analytical column was a Waters Xterra RP18, 5 μm, 250×4.6 mm, and the guard column was a Waters Xterra RP18, 5 μm, 20×3.9 mm. Mobile phase A was a mixture of 90% 0.05 M ammonium acetate buffer at pH 5.5 and 10% acetonitrile. Mobile phase B was a mixture of 10% 0.05 M ammonium acetate buffer at pH 5.5 and 90% acetonitrile. The solvent gradient is shown in Table 6.

TABLE 6

| time (min) | % A | % B |
| --- | --- | --- |
| 0 | 80 | 20 |
| 15 | 80 | 20 |
| 40 | 50 | 50 |
| 41 | 20 | 80 |
| 46 | 20 | 80 |
| 47 | 80 | 20 |
| 60 | 80 | 20 |

Flow rate was 1 mL/min, injection volume 30 μL, room temperature, 435 nm detection. Under these conditions, the peak due to the maleate salt has a retention time of about 24 minutes. Impurities are characterized by their relative retention time (RRT). The impurity at RRT=0.26 is the E isomer. The other impurities were not characterized.

Enantiomeric purity was determined by HPLC, using a Chiralpak AD analytical column, 10 μm, 250×4.6 mm (Daicel Chemical Industries, Ltd.) using an oven temperature of 30° C., a mobile phase of 2-propanol/heptane/diethylamine (50/50/0.1), an isocratic elution mode, a flow rate of 0.5 mL/min, injection volume of 50 μL, detector wavelength of 265 nm, dilution solvent 2-propanol/heptane (50/50) and a sample concentration of 0.3 mg/mL. Under these conditions, the S isomer has a retention time of about 15.5 minutes, and the R isomer has a retention time of about 22 minutes.

Water content was determined according to USP 25, <921>, Method Ic.

The results are shown in Tables 7–10.

TABLE 7

Sample A, at 25° C. and 60% Relative Humidity

|  | Initial | 1 mo. | 3 mo. | 6 mo. | 9 mo. | 12 mo. |
| --- | --- | --- | --- | --- | --- | --- |
| Appearance |  | U[a] | U[a] | U[a] | U[a] | U[a] |
| Assay (% free base equivalent) | 98.7 | 97.5 | 98.4 | 98.4 | 98.4 | 98.2 |
| Impurities (%) |  |  |  |  |  |  |
| RRT 0.26 | 0.09 | 0.28 | 0.05 | 0.07 | 0.15 | 0.06 |
| RRT 0.51 | 0.40 | 0.41 | 0.40 | 0.42 | 0.36 | 0.33 |
| RRT 0.71 | 0.05 | 0.06 | nd[b] | nd[b] | nd[b] | nd[b] |
| RRT 1.53 | 0.10 | 0.11 | 0.12 | 0.12 | 0.12 | 0.13 |
| RRT 1.74 | 0.09 | 0.10 | 0.09 | 0.09 | 0.07 | 0.07 |
| RRT 1.84 | 0.10 | 0.13 | 0.12 | 0.12 | 0.10 | 0.11 |
| Total Impurities (%) | 0.83 | 1.09 | 0.78 | 0.82 | 0.77 | 0.70 |
| Enantiomeric Purity (%) | >99.9 | >99.9 | >99.9 | >99.9 | >99.9 | >99.9 |
| Water Content (%) | 0.55 | 0.53 | 0.68 | 0.46 | 0.42 | 0.74 |

[a]unchanged
[b]not detected

TABLE 8

Sample A, at 40° C. and 75% Relative Humidity

|  | Initial | 1 mo. | 3 mo. | 6 mo. |
| --- | --- | --- | --- | --- |
| Appearance |  | U[a] | U[a] | U[a] |
| Assay (% free base equivalent) | 98.7 | 97.9 | 98.5 | 98.0 |
| Impurities (%) |  |  |  |  |
| RRT 0.26 | 0.09 | 0.29 | 0.05 | 0.07 |
| RRT 0.51 | 0.40 | 0.39 | 0.40 | 0.40 |
| RRT 0.71 | 0.05 | nd[b] | nd[b] | nd[b] |
| RRT 1.53 | 0.10 | 0.11 | 0.14 | 0.15 |
| RRT 1.74 | 0.09 | 0.08 | 0.08 | 0.07 |
| RRT 1.84 | 0.10 | 0.13 | 0.12 | 0.12 |
| Total Impurities (%) | 0.83 | 1.00 | 0.80 | 0.81 |
| Enantiomeric Purity (%) | 100.00 | 100.00 | 100.00 | 100.00 |
| Water Content (%) | 0.55 | 0.57 | 0.69 | 0.42 |

[a]unchanged
[b]not detected

TABLE 9

Sample B, at 25° C. and 60% Relative Humidity

|  | Initial | 1 mo. | 3 mo. | 6 mo. |
|---|---|---|---|---|
| Appearance |  | U[a] | U[a] | U[a] |
| Assay (% free base equivalent) | 97.8 | 98.2 | 98.2 | 97.7 |
| Impurities (%) |  |  |  |  |
| RRT 0.26 | 0.21 | 0.06 | 0.18 | 0.05 |
| RRT 0.51 | 0.68 | 0.62 | 0.61 | 0.56 |
| RRT 0.71 | 0.07 | 0.09 | 0.09 | 0.05 |
| RRT 1.53 | 0.11 | 0.09 | 0.08 | 0.08 |
| RRT 1.74 | 0.07 | 0.06 | 0.05 | 0.06 |
| RRT 1.84 | 0.10 | 0.08 | 0.09 | 0.09 |
| Total Impurities (%) | 1.24 | 1.00 | 1.10 | 0.90 |
| Enantiomeric Purity (%) | >99.90 | nm[b] | nm[b] | nm[b] |
| Water Content (%) | 0.45 | 0.50 | 0.54 | 0.47 |

[a]unchanged
[b]not measured

TABLE 10

Sample B, at 40° C. and 75% Relative Humidity

|  | Initial | 1 mo. | 3 mo. | 6 mo. |
|---|---|---|---|---|
| Appearance |  | U[a] | U[a] | U[a] |
| Assay (% free base equivalent) | 97.8 | 98.2 | 97.2 | 97.5 |
| Impurities (%) |  |  |  |  |
| RRT 0.26 | 0.21 | 0.13 | 0.18 | 0.05 |
| RRT 0.51 | 0.68 | 0.61 | 0.58 | 0.54 |
| RRT 0.71 | 0.07 | 0.08 | 0.08 | nd[b] |
| RRT 1.53 | 0.11 | 0.10 | 0.09 | 0.10 |
| RRT 1.74 | 0.07 | 0.06 | 0.05 | 0.05 |
| RRT 1.84 | 0.10 | 0.08 | 0.09 | 0.09 |
| Total Impurities (%) | 1.24 | 1.06 | 1.06 | 0.83 |
| Enantiomeric Purity (%) | >99.95 | nm[c] | nm[c] | >99.9 |
| Water Content (%) | 0.45 | 0.49 | 0.49 | 0.47 |

[a]unchanged
[b]not detected
[c]not measured

Example 3

Crystal form stability was assessed for samples of 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide maleate salt, polymorph Form 1, polymorph Form 2, and a mixture of polymorph Form 1 and Form 2. In each case, a sample of the substance was placed into a controlled temperature and humidity stability chamber at 40° C. and 75% relative humidity. Samples were taken several times during the duration of the test and analyzed for qualitative changes in the PXRD patterns. For Form 1, the duration of the test was 163 days, and no crystal form changes were observed in the PXRD pattern. For Form 2, the duration of the test was 134 days, and no crystal form changes were observed in the PXRD pattern. For the mixed Form 1/Form 2, the duration of the test was 6 weeks, and no crystal form changes were observed in the PXRD pattern.

Example 4

A six-week stability study was carried out on samples of 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide maleate salt, polymorph Form 1. The compound was exposed for 6 weeks, closed vial, at three stability test conditions: 5° C., 25° C./60% relative humidity and 40° C./75% relative humidity, and analyzed for chemical and enantiomeric stability as described in Example 2, except that the HPLC instrument was an Agilent 1100 series. The HPLC results are shown in Table 11.

TABLE 11

| Conditions | Recovery (%) | Total Impurity (%) |
|---|---|---|
| 5° C. ± 3° C. | 98.00 | 1.67 |
| 25° C. ± 2° C., 60% RH[a] | 97.52 | 1.85 |
| 40° C. ± 2° C.C, 76% RH[a] | 97.63 | 1.86 |

[a]relative humidity

The percent recovery was calculated based on the average response factor obtained from a reference standard throughout the HPLC run, and considering the E isomer as the compound and not as an impurity. Compounds in this class exhibit reversible E-Z isomerization, with the Z-isomer generally favored. The isomerization is often an artifact of sample preparation and analysis. Thermogravimetric analysis (TGA) showed minimal water content, and it was not considered in the percent recovery calculation. The values shown in the table are averages of several injections.

To determine the thermal stability and residual solvent content, the same samples were analyzed by DSC and TGA. The results are shown in Table 12.

TABLE 12

|  |  | TGA | | DSC | |
|---|---|---|---|---|---|
| Sample | Conditions | Wt. Loss (%), 25° C.–125° C. | Wt. Loss (%), 25° C.–275° C. | Peak 1 (° C.) | Enthalpy (J/g) |
| maleate salt | 5° C. | 1.44 | 23.15 | 206.5 | 224.0 |
| maleate salt | 25° C./60% RH[a] | 1.36 | 24.36 | 209.1 | 253.7 |
| maleate salt | 40° C./75% RH[a] | 1.66 | 20.61 | 208.3 | 243.3 |

[a]relative humidity

The 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide maleate salt was stable under all stability conditions investigated. The assay of the 6-week stability samples was 97.1–98.5% with a total impurity content of 1.67–1.85%. The assay and impurity profiles did not show significant change compared to the initial profiles under all conditions studied. HPLC quantitative analysis for maleic acid was consistent with the stoichiometric ratio of free base to acid of 1:1 (data not shown). Also, there was no chiral transformation observed in any samples. Enantiomeric stability was also confirmed in samples held at 80° C. for 2 weeks, with no increase in the amount of R isomer observed.

DSC analysis of the 6-week samples showed a single sharp endothermic melt/decomposition peak at 207–208° C. TGA analysis showed a minimal weight loss (less than 2%) between 25–125° C. Significant weight loss (about 21-23%) occurred at 207° C., corresponding to the endothermic peak at 218° C. observed by DSC.

PXRD analysis of the 6-week samples maintained at 40° C./75% RH showed no crystalline changes compared to a control sample.

Example 6

Figure 8:
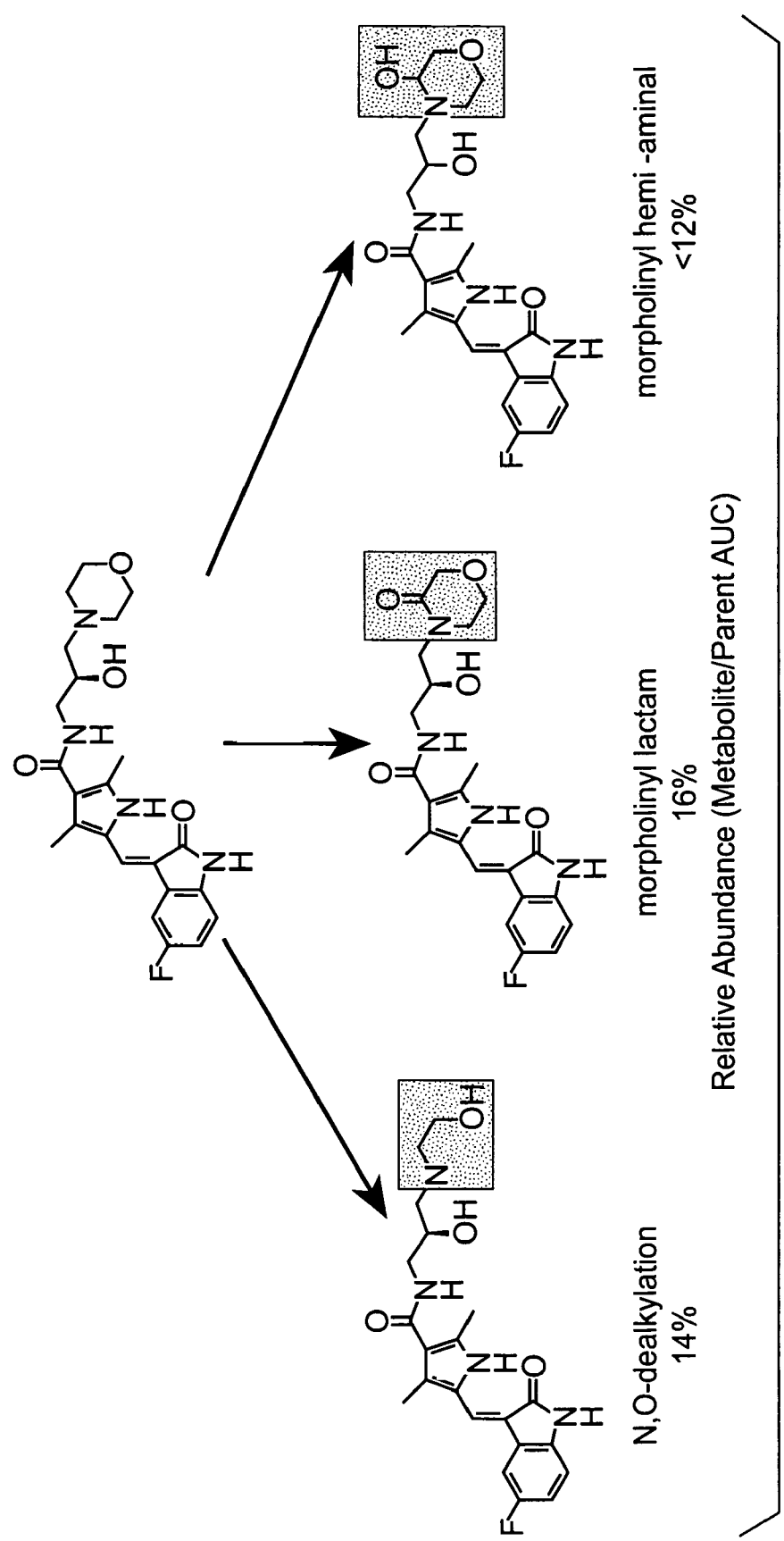
FIG. 8 shows the structural formulae of 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide and the relative abundance of three metabolites in monkey plasma.
Figure 9:
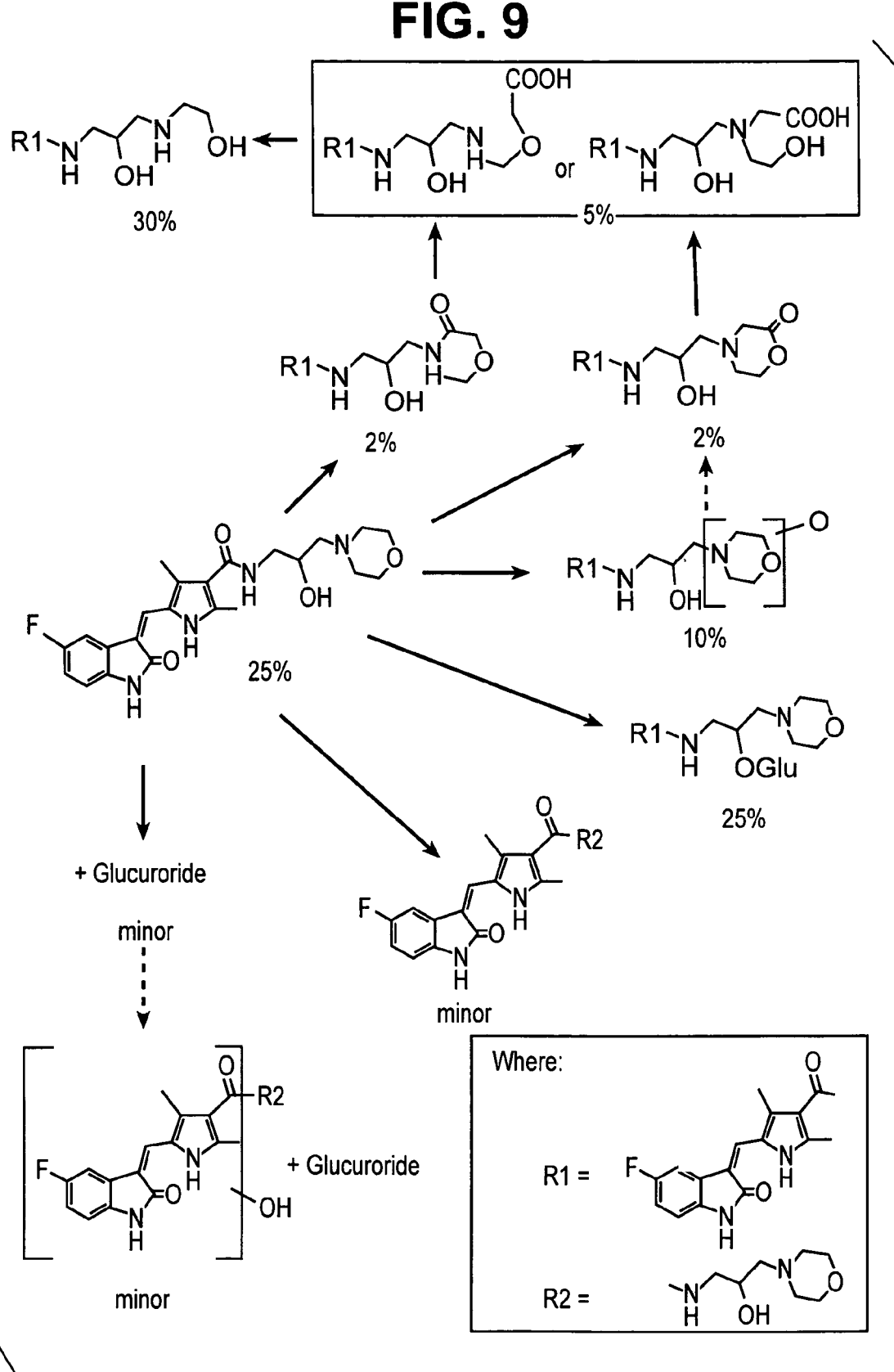
FIG. 9 shows the structural formulae of 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide and the relative abundance of several metabolites in human urine.

In preclinical species (in vivo and in vitro) and in human hepatocytes and microsomes, 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide metabolism proceeds primarily through an oxidative pathway mediated by hepatic cytochrome P450. The primary site of metabolism is the morpholinyl group. Three metabolites have been identified in vivo following single oral administration (100 mg/kg) to cynomolgus monkeys (FIG. 8). These 3 metabolites, which were detected at <16% relative abundance to parent in monkey plasma, were also the major products observed in human microsomes and hepatocytes. Relative abundance was determined from monkey plasma following a single dose of 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide (100 mg/kg) and based on ($AUC_{0-12}$ metabolite/$AUC_{0-12}$ parent)×100, estimated from the characteristic indole UV absorption at 440 nM. The N,O-dealkylation metabolite has been confirmed via nuclear magnetic resonance (NMR). This metabolite has biochemical, but not cellular, activity, suggesting that it lacks adequate permeability to enter cells. The morpholinyl lactam metabolite is the product of oxygenation-dehydrogenation and has also been confirmed via NMR. The morpholinyl hemi-aminal metabolite is an unstable metabolite identified via an iminium-ion trapping experiment. Metabolites were also determined in human urine, following a single 12.5 mg dose; these metabolites are shown in FIG. 9. Relative abundance was determined by UV response at 428 nm.

While the invention has been illustrated by reference to specific and preferred embodiments, those skilled in the art will recognize that variations and modifications may be made through routine experimentation and practice of the invention. Thus, the invention is intended not to be limited by the foregoing description, but to be defined by the appended claims and their equivalents.

We claim:

1. A crystalline anhydrous maleate salt of 5-[(Z)-(5-fluoro-2-oxo-1,2-dihydro-3H-indol-3-ylidene) methyl]-N-[(2S)-2-hydroxy-3-morpholin-4-ylpropyl]-2,4-dimethyl-1H-pyrrole-3-carboxamide.

2. The maleate salt of claim 1, wherein the salt has a powder X-ray diffraction pattern comprising peaks at diffraction angles (2θ) of 12.7 and 15.4.

3. The maleate salt of claim 1, wherein the salt has a powder X-ray diffraction pattern comprising peaks at diffraction angles (2θ) of 13.1 and 15.9.

4. The maleate salt of claim 1, wherein the salt has a powder X-ray diffraction pattern comprising peaks at diffraction angles (2θ) of 12.7, 13.1, 15.4 and 15.9.

5. A crystalline anhydrous maleate salt of 5-[(Z)-(5-fluoro-2-oxo-1,2-dihydro-3H-indol-3-ylidene) methyl]-N-[(2S)-2-hydroxy-3-morpholin-4-ylpropyl]-2,4-dimethyl-1H-pyrrole-3-carboxamide having a powder X-ray diffraction pattern comprising peaks at diffraction angles (2θ) essentially the same as shown in FIG. 1.

Figure 2:
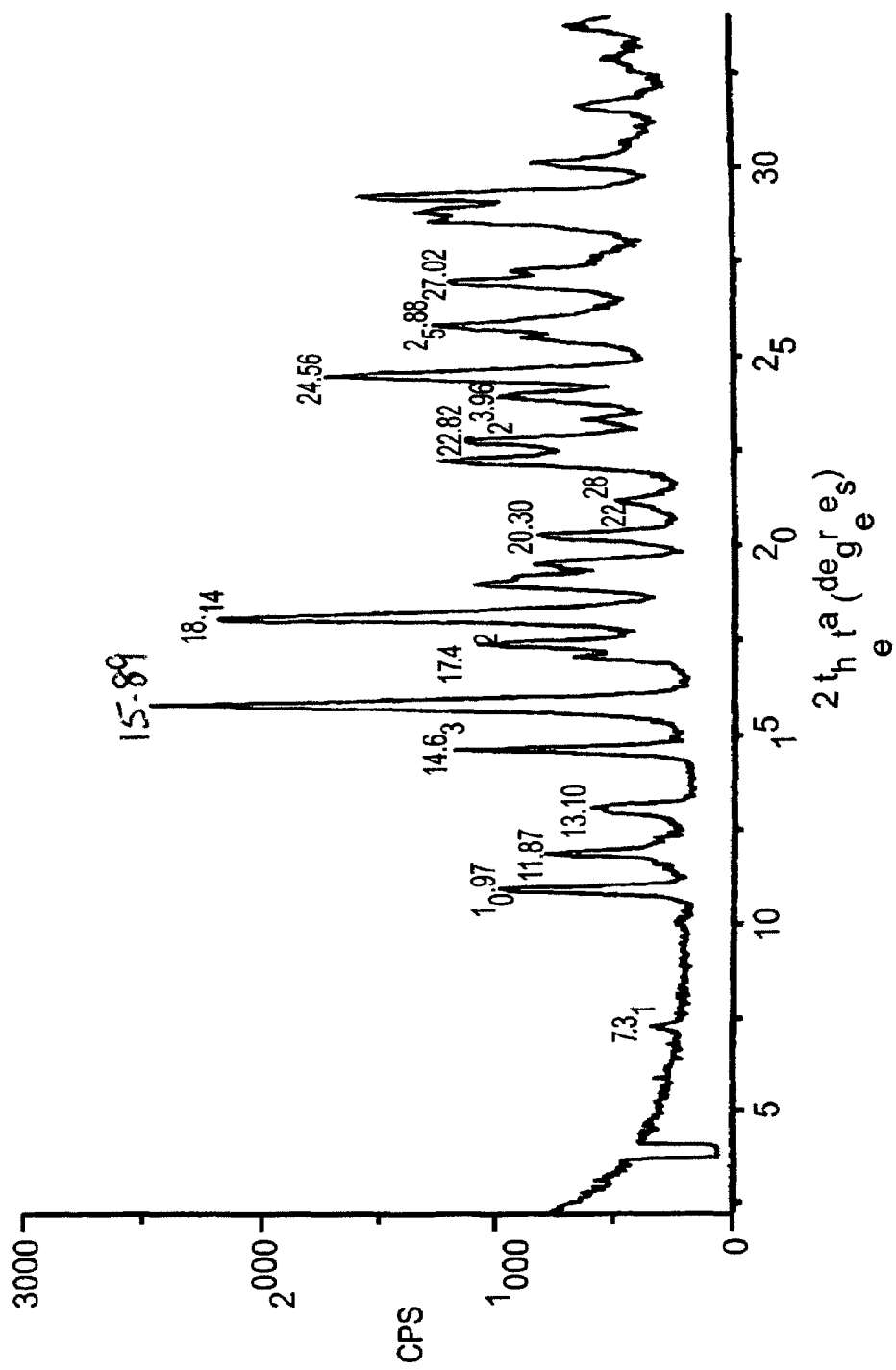
FIG. 2 shows a powder X-ray diffraction pattern of a maleate salt of 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide, polymorph Form 2.

6. A crystalline anhydrous maleate salt of 5-[(Z)-(5-fluoro-2-oxo-1,2-dihydro-3H-indol-3-ylidene) methyl]-N-[(2S)-2-hydroxy-3-morpholin-4-ylpropyl]-2,4-dimethyl-1H-pyrrole-3-carboxamide having a powder X-ray diffraction pattern comprising peaks at diffraction angles (2θ) essentially the same as shown in FIG. 2.

7. A pharmaceutical composition comprising the salt of claim 1.

8. A pharmaceutical composition comprising the salt of claim 5.

9. A pharmaceutical composition comprising the salt of claim 6.

* * * * *